(12) United States Patent
Han et al.

(10) Patent No.: US 12,378,508 B2
(45) Date of Patent: Aug. 5, 2025

(54) ORGAN-ON-CHIPS THAT MIMIC HUMAN PREGNANCY AND PARTURITION

(71) Applicants: The Texas A&M University System, College Station, TX (US); Board of Regents, The University of Texas System, Austin, TX (US)

(72) Inventors: Arum Han, College Station, TX (US); Sungjin Kim, Bryan, TX (US); Ramkumar Menon, League City, TX (US); Lauren Richardson, College Station, TX (US); Ourlad Alzeus Tantengco, Bataan (PH)

(73) Assignee: The Texas A&M University System, College Station, TX (US)

( * ) Notice: Subject to any disclaimer, the term of this patent is extended or adjusted under 35 U.S.C. 154(b) by 930 days.

(21) Appl. No.: 17/336,730

(22) Filed: Jun. 2, 2021

(65) Prior Publication Data
US 2022/0002646 A1    Jan. 6, 2022

Related U.S. Application Data

(60) Provisional application No. 63/033,512, filed on Jun. 2, 2020.

(51) Int. Cl.
*C12M 3/00* (2006.01)
*C12M 1/00* (2006.01)
(Continued)

(52) U.S. Cl.
CPC ............ *C12M 21/08* (2013.01); *C12M 23/16* (2013.01); *C12M 25/02* (2013.01); *C12M 29/10* (2013.01); *C12M 33/00* (2013.01)

(58) Field of Classification Search
CPC ...... C12M 21/08; C12M 23/16; C12M 23/58; C12M 25/02; C12M 29/10; C12M 33/00; C12M 35/08; C12M 41/46
See application file for complete search history.

(56) References Cited

U.S. PATENT DOCUMENTS

| | | | |
|---|---|---|---|
| 2009/0088342 A1* | 4/2009 | Moraes | C12M 25/04 506/12 |
| 2012/0276622 A1* | 11/2012 | Wu | C12M 25/02 435/289.1 |

(Continued)

FOREIGN PATENT DOCUMENTS

WO    WO-2013086329 A1 *    6/2013    ........ B01L 3/502715

*Primary Examiner* — Michael L Hobbs
(74) *Attorney, Agent, or Firm* — Jackson Walker, LLP

(57) ABSTRACT

In an embodiment, the present disclosure pertains to an organ-chip model having a plurality of cell culture chambers connected through arrays of microfluidic channels. In some embodiments, each cell culture chamber of the plurality of cell culture chambers include an inlet and an outlet. In some embodiments, the inlet is configured to receive at least one of a cell, cell media, or a cell stimulant. In some embodiments, at least one outlet is configured to collect effluent. In some embodiments, the organ-chip model can include, without limitation, an organ-chip model of amnion membrane, an organ-chip model of a feto-maternal interface (fetal membrane-decidua parietalis), an organ-chip model of a feto-maternal interface (placenta-decidua interface), an organ-chip model of a cervix, and combinations thereof. In some embodiments, the organ-chip model is an interconnected organ-chip model having a combination of one or more organ-chip models with interconnected cell culture chambers.

21 Claims, 28 Drawing Sheets

(51) Int. Cl.
*C12M 1/12* (2006.01)
*C12M 1/26* (2006.01)
*C12M 3/06* (2006.01)

(56) References Cited

U.S. PATENT DOCUMENTS

2015/0087006 A1* 3/2015 Pak .................. G01N 33/54366
 435/287.1
2015/0377861 A1* 12/2015 Pant ....................... C12M 23/34
 435/395

* cited by examiner

1. AEC Cont Outer Chamber
2. AEC Cont in Tunnel
3. AEC Cont Inner Chamber

1. AEC CSE Outer Chamber
2. AEC CSE in Tunnel
3. AEC CSE Inner Chamber

1. AMC CSE Inner Chamber
2. AMC CSE in Tunnel
3. AMC CSE Outer Chamber

ORGAN-ON-CHIPS THAT MIMIC HUMAN PREGNANCY AND PARTURITION

CROSS-REFERENCE TO RELATED APPLICATIONS

This patent application claims priority from, and incorporates by reference the entire disclosure of, U.S. Provisional Application 63/033,512 filed on Jun. 2, 2020.

STATEMENT REGARDING FEDERALLY SPONSORED RESEARCH

This invention was made with government support under R01 HD100729 awarded by the Eunice Kennedy Shriver National Institute of Child Health and Human Development. The government has certain rights in the invention.

TECHNICAL FIELD

The present disclosure relates generally to human pregnancy and parturition and more particularly, but not by way of limitation, to organ-on-chips that mimic human pregnancy and parturition.

BACKGROUND

This section provides background information to facilitate a better understanding of the various aspects of the disclosure. It should be understood that the statements in this section of this document are to be read in this light, and not as admissions of prior art.

Fetal membranes (amniochorionic membrane or placental membranes) are the innermost lining of the intrauterine cavity that surrounds the fetus and provides mechanical and immune protection throughout gestation. Membrane homeostasis is advantageous for the maintenance of pregnancy and fetal growth. Compromise in the fetal membrane's structural, biologic, and mechanical functions or chorioamniotic inflammation are often associated with spontaneous preterm birth and preterm premature rupture of the fetal membranes, two major complications of pregnancy that affect more than 9.6% of all cases in the United States alone and 11% worldwide. However, mechanisms that maintain the fetal membrane's homeostasis during gestation and factors contributing to the loss of its functional ability, which could predispose membranes to labor-associated inflammatory changes at term (physiologic) or preterm (pathologic), are still unclear. A clear understanding of these mechanisms will help fill a major knowledge gap regarding the role of fetal membranes in term and preterm labor, as well as lead to designing better strategies to reduce membrane-associated adverse outcomes.

SUMMARY OF THE INVENTION

This summary is provided to introduce a selection of concepts that are further described below in the Detailed Description. This summary is not intended to identify key or essential features of the claimed subject matter, nor is it to be used as an aid in limiting the scope of the claimed subject matter.

In an embodiment, the present disclosure pertains to an organ-chip model having a plurality of cell culture chambers connected through arrays of microfluidic channels. In some embodiments, each cell culture chamber of the plurality of cell culture chambers have an inlet and an outlet. In some embodiments, the inlet is configured to receive at least one of a cell, cell media, or a cell stimulant. In some embodiments, at least one outlet is configured to collect effluent. In some embodiments, the organ-chip model can include, without limitation, an organ-chip model of amnion membrane, an organ-chip model of a feto-maternal interface (fetal membrane-decidua parietalis), an organ-chip model of a feto-maternal interface (placenta-decidua interface), an organ-chip model of a cervix, and combinations thereof.

In some embodiments, the organ-chip model further includes a bottom substrate. In some embodiments, the bottom substrate is a flexible membrane to allow for application of a stretching motion to cells during culture. In some embodiments, the organ-chip model is an interconnected organ-chip model. In some embodiments, the interconnected organ-chip model includes a combination of one or more organ-chip models connected through a plurality of microfluidic channels. In some embodiments, the plurality of microfluidic channels interconnect between cell culture chambers in the one or more organ-chip models. In some embodiments, each cell culture chamber of the plurality of cell culture chambers has a shape that can include, without limitation, a circular shape, an oval shape, a rectangular shape, a ring-shape, a curve shape, and combinations thereof.

In some embodiments, at least one microfluidic channel of the arrays of microfluidic channels is in fluid communication with at least one cell culture chamber of the plurality of cell culture chambers. In some embodiments, each microfluidic channel of the arrays of microfluidic channels are sized to control movement. In some embodiments, the movement is at least one of preventing movement from one cell culture chamber to another cell culture chamber during an initial cell loading process, allowing biochemicals to diffuse through at least one cell culture chamber of the plurality of cell culture chambers, or allowing cells to migrate from one cell culture chamber to another cell culture chamber. In some embodiments, number and dimension of the arrays of microfluidic channels are adjusted to control diffusion time between the plurality of cell culture chambers.

In some embodiments, the at least one of a cell, cell media, or a cell stimulant is perfused through a syringe pump connected to an inlet of one cell culture chamber and the effluent is collected from an outlet of another cell culture chamber. In some embodiments, the at least one outlet configured to collect effluent is configured such that the effluent can be collected at different time points. In some embodiments, cell culture media and collection reservoirs are utilized such that passive diffusion can provide the cell culture media to cells. In some embodiments, each cell culture chamber of the plurality of cell culture chambers are configured to be filled to different heights to allow control over diffusion.

In some embodiments, the organ-chip model further includes an additional layer having at least one culture media reservoir integrated on top of the organ-chip model, In some embodiments, the at least one culture media reservoir has an inlet and outlet aligned together. In some embodiments, the at least one culture media reservoir is configured to be periodically filled with at least one of new culture media or biochemicals. In some embodiments, the biochemicals can include, without limitation, drugs, harmful substances, and combinations thereof.

In some embodiments, fluorescent tagging of cells being grown in the organ-chip model is conducted to visualize cells migrating between the plurality of cell culture chambers. In some embodiments, immunostaining of cells within the organ-chip model is conducted via loading biochemicals for immunostaining of the cells through at least one inlet or a culture media reservoir. In some embodiments, one cell culture chamber is loaded with one cell-type and another cell culture chamber is loaded with another cell-type. In some embodiments, the cell-type can include, without limitation, amnion epithelial cells (AEC), amnion mesenchymal cells (AMC), chorion mesenchymal cells (CMC)/chorion trophoblast (CT), decidua parietalis cells, and combinations thereof. In some embodiments, at least one microfluidic channel of the arrays of microfluidic channels is filled with extracellular matrixes.

In some embodiments, the plurality of cell culture chambers includes at least two cell culture chambers. In some embodiments, the plurality of cell culture chambers includes at least four cell culture chambers.

BRIEF DESCRIPTION OF THE DRAWINGS

A more complete understanding of the subject matter of the present disclosure may be obtained by reference to the following Detailed Description when taken in conjunction with the accompanying Drawings wherein:

FIG. 1A shows a schematic illustration of the AM-OOC. Three-dimensional (3D) and cross-sectional view showing the physical isolation of AECs and AMCs in each culture chamber, connected by 24 microchannels filled with type IV collagen. FIG. 1B shows a cross-sectional view showing the principle of diffusion barrier formation by liquid height difference. FIG. 1C shows microfabrication and assembly steps for the AM-OOC device. Two layers of photosensitive epoxy (SU-8) with different thicknesses were patterned on top of a silicon substrate to form the microchannels, and the 2 cell culture chambers (outer chamber: AECs; inner chamber: AMCs). Polydimethylsiloxane (PDMS) devices were replicated from the SU-8 master using soft lithography process, and 7-mm diameter reservoirs were punched out followed by bonding onto poly-D-lysine- or Matrigel-coated substrates. FIG. 1D shows each AM-OOC fits into 1 well of a conventional 6-well polystyrene culture plate.

FIG. 2A-FIG. 2B shows the condition where the inner chamber fluid level is higher than that of the outer chamber fluid level, countering diffusion from outside to inside. Brightfield and fluorescence microscopy images showed FITC diffusing through microchannels without type IV collagen coating. FIG. 2A shows a graph illustrating the degree of FITC diffusion from the outside chamber to the inside chamber. FIG. 2B shows a repeat of FIG. 2A, but when the microchannels in the AM-OCC is filled with type IV collagen. FIG. 2C-FIG. 2D shows the condition where the outer chamber fluid level is higher than that of the inner chamber fluid level, countering diffusion from inside to outside. Brightfield and fluorescence microscopy images showed FITC diffusing through microchannels without type IV collagen coating. FIG. 2C shows a graph illustrating the degree of FITC diffusion from the inside chamber to the outside chamber. FIG. 2D shows repeat of FIG. 2C, but when the microchannels in the AM-OCC is filled with type IV collagen.

FIG. 3A shows analysis of confocal images of native levels of vimentin and cytokeratin-18 (CK-18) expression in AECs and AMCs (AEC: 0.56±0.02 vs. AMC: 1.1±0.02; n=3). AECs are in a metastate, meaning they co-express both epithelial and mesenchymal markers. AMCs had significantly higher vimentin:CK-18 levels compared with AECs (P>0.0001; n=3). Blue, 4',6-diamidino-2-phenylindole (DAPI); green, vimentin; red, CK-18. Values are expressed as mean intensities±SEM. FIG. 3B shows analysis of bright field microscopy images showing that AECs migrate into the opposite chamber more frequently than AMCs. Values are expressed in number of migrated cells in each device (P=0.0064). FIG. 3C shows analysis of confocal images of native and oxidative stress (OS) induced cigarette smoke extract (CSE) levels of vimentin and CK-18 expression in AECs (AEC control: 0.56±0.02, CSE: 0.67±0.02) and AMCs (AMC control: 1.1±0.2, CSE: 1.1±0.2; N=3). CSE AECs had significantly higher vimentin:CK-18 levels compared with AEC controls (P=0.02), whereas AMC intermediate filament expression remained constant regardless of treatment (n=3). Blue, DAPI; green, vimentin; red, CK-18. Values are expressed as mean intensities±SEM. FIG. 3D shows analysis of bright field microscopy images showing that CSE treatment inhibited migration of AECs compared with AEC controls (P=0.0005), whereas CSE treatment of AMCs stimulated migration (n=3). Control AECs contain the most migratory potential of all treatments and cell types. Migratory cells were defined as cells that had migrated through the microchannel and were now resident in the opposite chamber.

FIG. 4A (schematic representation) and FIG. 4B show AECs in the outer chamber under native conditions express basal levels of vimentin:CK-18 ratio (0.5±0.01), perinuclear vimentin, and an epithelial morphology. Migration of AECs is accompanied by a significant increase of vimentin:CK-18 ratio (0.62±0.02; P=0.0025), vimentin's relocalization to the leading edge, and an elongated mesenchymal morphology indicative of an epithelial-mesenchymal transition (EMT). Once AECs completely migrated to the inner chamber, they reverted back to basal expression of vimentin:CK-18 ratio (0.48±0.02; P=0.0009), perinuclear vimentin, and an epithelial morphology indicative of a mesenchymal-epithelial transition (MET). FIG. 4C (schematic representation) and FIG. 4D show AECs in the outer chamber under OS conditions (CSE) express relatively high levels of vimentin:CK-18 ratio (0.65±0.02) compared with control AECs. Additionally, AECs treated with CSE contained vimentin localization at the leading edge and an elongated mesenchymal morphology. Migration of CSE-treated AECs is not accompanied by changes in the vimentin:CK-18 ratio (0.58±0.03), vimentin relocalization, or morphology variations, which shows that CSE maintains AECs in a static state of EMT. However, the few AECs able to cross the microchannels did, under MET transitions, revert to basal expression of vimentin:CK-18 ratio (0.3±0.02; P=0.0004), very little vimentin, and an epithelial morphology. FIG. 4E (schematic representation), FIG. 4F, FIG. 4G (schematic representation), and FIG. 4H show AMCs in the inner chamber under native and OS conditions express relatively high levels of vimentin:CK-18 ratio (control: 1.1±0.2 and CSE: 1.1±0.2) compared with AECs regardless of treatment. Migrating AMCs maintain their vimentin:CK-18 (control: 1.0±0.03, CSE: 1.1±0.09) while relocalizing vimentin to the leading edge and inducing an elongated cell morphology. Migration of AMCs into the outer chamber significantly increases the vimentin:CK-18 ratio (control: 2.1±0.14, CSE: 2.4±0.2), while also inducing native vimentin localization and mesenchymal morphology.

FIG. 5A shows a schematic representing AEC and AMC cellular transitions; arrows highlight migration direction. Confocal images were captured at original magnification, 310. FIG. 5B shows analysis of bright field microscopy images shows AECs treated with CSE, in coculture, migrated into the opposite chamber more frequently than the AEC control (AEC control: 5.1±0.06, CSE: 7.3±0.3) (AEC: bar 1 vs. 2; 1.5-fold increase) (AMC: bar 1 vs. 3; 2-fold increase). CSE treatment of AMCs did not affect AECs' migration (5.1±0.06 vs. 4.3±0.8). CSE cotreatment of AECs and AMCs inhibited AECs' migration (0.67±0.6), whereas cotreatment with CSE+ relieved the effects of CSE (1.3±0.8) (AECs: CSE/CSE vs. CSE+/CSE+=2-fold higher) (AMC: CSE/CSE vs. CSE+/CSE+=2.5-fold higher). Values are expressed as mean intensities±SEM. FIG. 5C shows analysis of bright field microscopy images shows AMCs treated with CSE, in coculture, migrated into the opposite chamber more frequently than the AMC control (AMC control: 2.7±0.6, CSE: 5.5±1.5). CSE treatment of AECs did not affect AMCs' migration (2.7±0.6 vs. 3.3±0.3). CSE cotreatment of AECs and AMCs inhibited AEC migration (1±0.5), whereas cotreatment with CSE+ relieved the effects of CSE (2.7±0.6). Values are expressed as mean intensities±SEM. Migratory cells were defined as cells that had migrated through the microchannel and identified by the opposite color of cell nuclei (i.e., green nuclei AEC cells in the red nuclei AMC population).

FIG. 6A shows enzyme-linked immunosorbent assay (ELISA)-measured media concentrations of granulocyte-macrophage colony-stimulating factor (GM-CSF) from the AEC (outer chamber) and AMC (inner chamber). Though not significant, AMCs naturally have a higher level of GM-CSF expression compared with AECs (AEC: 5.7±1.5 ng/ml, AMC: 2208±1629 ng/ml). FIG. 6B and FIG. 6C show CSE treatment, regardless to which chamber, induced higher expression of GM-CSF in AMCs compared with AECs (CSE AMCs' effect on control AECs, control/control: 5.7±1.5, control/CSE: 8.2±2.4) (FIG. 6B) (CSE AECs' effect on AMCs, control/control: 2208±1629, CSE/control: 3835±1541) (FIG. 6C). CSE+ treatment lowered GM-CSF in both AECs (2.8±0 ng/ml) and AMCs (81.9±43 ng/ml). Values are expressed as mean intensities±SEM.

FIG. 15A shows two-dimensional (2D) schematic of the multi-organ feto-maternal interface organ-on-chip (PI-FMI-OOC) model containing cells from both placenta and fetal membrane interfaces. The two interfaces are connected by an array of microchannels at the maternal decidua layer (basalis and parietalis). FIG. 15B shows a 3D drawing of coculture chambers having independent inlets/outlets. The PI-FMI-OOC can have an on-chip reservoir array layer integrated on top of the device that contains a single drug reservoir to mimic maternal blood treatment of both decidua components in utero.

FIG. 17A shows ELISA-measured media concentrations of interleukin-8 (IL-8) from the AEC and AMC in 2D culture vs Am-OOC culture. Culturing AECs and AMCs in the AM-OOC innately induced more IL-8 than 2D cultures (N=3). **=P<0.0001. =P=0.001. FIG. 17B shows AECs naturally express very low levels of GM-CSF in the AM-OOC devices (Control: 3.2±0.35 ng/ml; CSE: 4.6±0.9 ng/ml; N=3), and do not propagate GM-CSF into the inner chamber even after 48 hours. Values are expressed as mean intensity±SEM. FIG. 17C shows CSE treatment of AMCs induced GM-CSF production (Control: 99±26 ng/ml; CSE: 148±78 ng/ml: N=3) compared to controls, but without propagation of GM-CSF into the outer chamber even after 48 hours. Values are expressed as mean intensity±SEM.

DETAILED DESCRIPTION

Figure 1A:
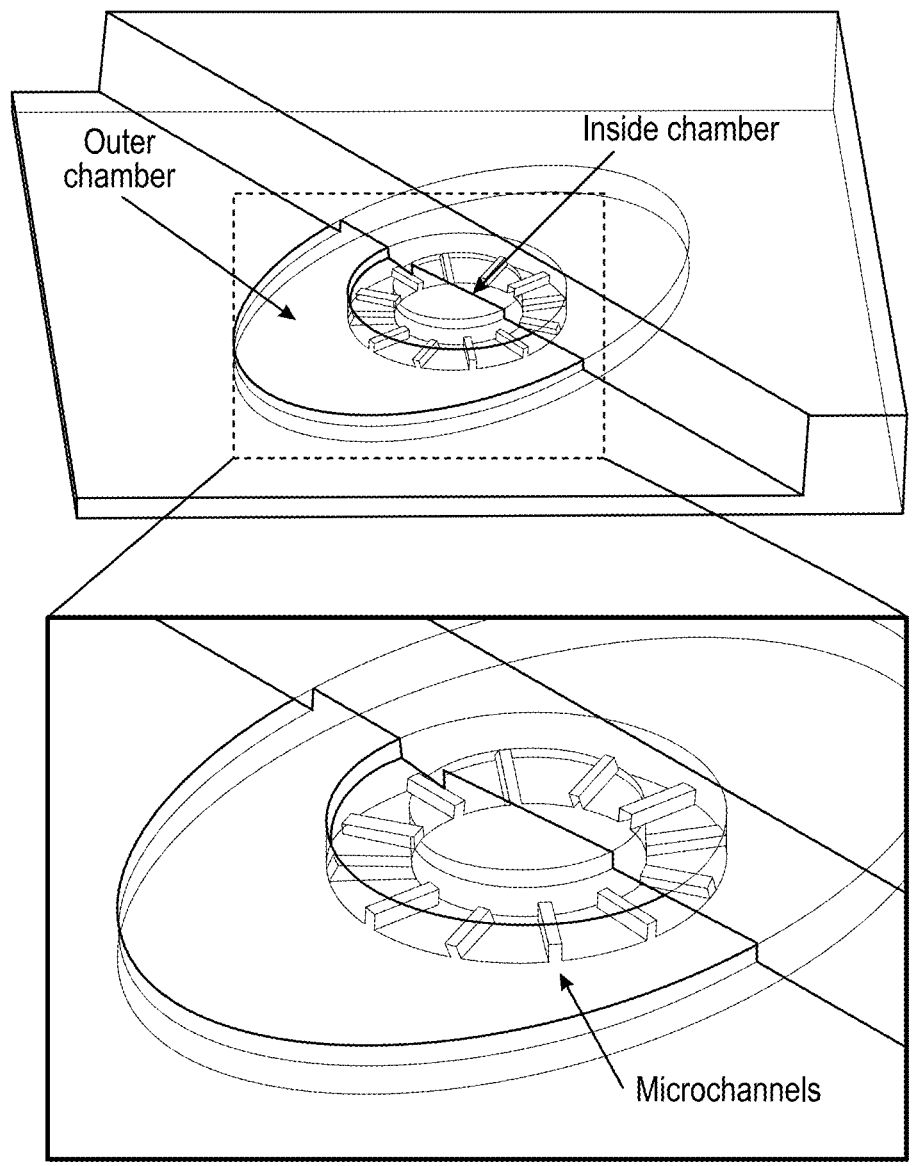
FIGS. 1A-1D illustrate amnion membrane-on-chip (AM-OOC) fabrication and layout according to aspects of the present disclosure. The AM-OOC is designed to recreate the amnion membrane in vitro by co-culturing amnion epithelial cells (AECs) and amnion mesenchymal cells (AMCs) separated by a type IV collagen-filled microfluidic channel array (mimicking basement membrane).

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

Fetal membranes are multilayer structures having amnion epithelial cells (AECs) and chorion trophoblasts connected by a collagen-rich extracellular matrix (ECM) that also contains amnion mesenchymal cells (AMCs). The amnion membrane is the most elastic component of the fetal membranes and is composed of an AEC type IV collagen-rich basement membrane with AMCs embedded in ECM. Additionally, the amnion membrane bears a majority of the tensile strength to mechanically keep the tissue intact throughout gestation. AECs and AMCs also provide immune and endocrine functions that are used in the maintenance of pregnancy. Membrane growth and remodeling occur during gestation and involve both cellular transitions and collagenolytic matrix turnover. Cellular-level changes primarily involve AECs and AMCs that are conventionally considered as purely epithelial and mesenchymal in physiognomies. However, recent findings suggest that AECs and AMCs are pluripotent stem cells in a metastate in which they coexpress both epithelial and mesenchymal markers. This metastate is thought to allow amnion membrane cells to readily undergo cellular transitions demanded by intrauterine microenvironmental cues to either promote membrane remodeling and maintain integrity during gestation or predispose them to weakening in preparation for labor and delivery.

The recent discovery of fetal membrane microfractures (MFs) highlights possible areas of such cellular transitions and remodeling. MFs are biologic interruptions in the amnion membrane characterized by AEC puckering or gaps, basement membrane degradation, and tunnels that extend into the collagen matrix with migrating cells. Increased number and morphometry (width and depth) of MFs at term and in preterm birth and preterm premature rupture of the fetal membranes suggest that persistence of MFs may indicate lack of remodeling and membrane dysfunction. Induction of oxidative stress (OS) in vitro in fetal membrane explants, similar to that seen at term and preterm parturitions, increases MFs, their morphometry, and their collagenolysis, supporting the hypothesis that the persistence of MFs may predispose membranes to dysfunctions and instability. This hypothesis was further supported by in vitro scratch assays (mimicking MFs). Data suggest that AECs can proliferate, migrate, transition, and heal wounds, supporting the hypothesis that MFs are likely areas where membrane remodeling occurs. Cell transitions at the scratch site include epithelial-to-mesenchymal transitions (EMTs) or the reverse mesenchymal-to-epithelial transitions (METs). Furthermore, OS prevented cellular transitions and healing and recapitulated similar observations associated with term and preterm parturitions.

Despite the recent finding that amnion cells can undergo cellular transitions, it is still unclear if MFs are formed or healed by fetal cells in vivo. Determining a causal relationship between cellular transitions and environmental stimulants will illuminate the role of fetal cells in membrane remodeling. However, studying such phenomena is extremely challenging because of the lack of available experimental approaches and models of the multicellular amnion membrane that can be experimentally manipulated and tested. Current experimental approaches of 2-dimensional (2D) single cell cultures, amnion cell-like organ explant cultures, and transwell coculture systems (of AMCs and AECs) are all insufficient to understand cellular transitions and their roles in tissue remodeling. Conventional mixed culture or coculture methods, where cells are cultured in randomly distributed form or in transwells, often fail to provide means to locally manipulate the physical and biochemical environments of each cell type in culture. Therefore, it is challenging to investigate the interactions between the fetal membrane cells, namely, AMCs and AECs, for detailed mechanistic studies. In addition, migratory cells that are thought to play an important role in collagen homeostasis cannot be easily monitored or studied using these methods. MFs and scratch assay experiments conducted and terminated at discrete time points may show a snapshot of cellular transition but do not convey the cellular mechanisms involved during the course of membrane remodeling; they also create challenges for understanding the dynamic cell-cell relationships.

To overcome the limitations of these traditional approaches, an amnion membrane organ-on-chip (AM-OOC) was developed, allowing for direct monitoring of amnion cell migration and transition under a coculture condition in which the two different cell types could be cultured in two different microenvironments while enabling the application of localized chemical cues to only one cell type. Microfluidic organ-on-chip (OOC) technologies allow for control and manipulation of multiple cell types and their microenvironments with high accuracy and have been demonstrated as a promising technology to achieve in vitro models that more physiologically mimic in vivo structures and functions. Recently, a fetal membrane OOC model was presented; however, this model lacks a degradable basement membrane as well as mesenchymal cells. Thus, the device does not accurately recapitulate how cells migrate through a basement membrane and also lacks critical factors from the mesenchymal cells. A truly physiologically relevant fetal membrane OOC model has the potential to recapitulate inter- and intracellular signaling and the physiologic context of tissue dynamics by compartmentalizing the major cellular components of a fetal membrane while still allowing interactions between these chambers. As a first step in establishing a full fetal membrane OOC system, the AM-OOC was initially developed and its usefulness in addressing the experimental limitations were tested. Using this OOC approach, AECs' and AMCs' migration and transitions independently were tested and compared, using AECs and AMCs harvested from human placenta, as well as when cultured together under normal and OS conditions. AECs can migrate, degrade basement collagen, and transition to become AMCs. OS induces AECs to undergo EMT and increase collagenolysis and inflammation. Additionally, the presence of AMCs accelerates this process. Conversely, AMCs migrate, degrade basement collagen, and transition to become epithelial cells in the presence of AECs. OS maintains AMCs' mesenchymal phenotype, promotes migration, degrades basement collagen, and propagates inflammation.

As discussed above, the amnion membrane that lines the human intrauterine cavity is composed of AECs connected to an extracellular matrix containing AMCs through a basement membrane. Cellular interactions and transitions are mechanisms that facilitate membrane remodeling to maintain its integrity. Dysregulation of cellular remodeling, primarily mediated by OS, is often associated with preterm birth. However, the mechanisms that maintain membrane homeostasis remain unclear. To understand these mechanisms, an AM-OOC was developed and the interactive and transition properties of primary human AECs and AMCs under normal and OS conditions were tested. The AM-OOC contained two chambers connected by type IV collagen—coated microchannels, allowing independent culture conditions that permitted cellular migration and interactions. Cells grown either independently or co-culture were exposed to OS inducing cigarette smoke extract, antioxidant N-acetyl-L-cysteine (NAC), or both. When grown independently, AECs transitioned to AMCs and migrated, whereas AMCs migrated without transition. OS caused AECs' transition but prevented migration, whereas AMCs' migration was unhindered. Co-culture of cells facilitated transition, migration, and eventual integration in the contiguous population. OS cotreatment in both chambers facilitated AECs' transition, prevented migration, and increased inflammation, a process that was prevented by NAC. The AM-OOC recapitulated cellular mechanisms observed in utero and enabled experimental manipulation of cells to determine their roles during pregnancy and parturition.

This basic two-chamber AM-OOC model was then expanded into a four-chamber feto-maternal interfaced OOC model that contains both feto and maternal components in the chip. The fetal membrane-decidua interface model (FMi-OOC) having four co-culture compartments interconnected through arrays of microfluidic channels. Here, three cell types from the fetal side (amnion epithelial cells [AEC], amnion mesenchymal cells [AMC], chorion mesenchymal cells [CMC]/chorion trophoblast [CT]) and one from the maternal side (decidua cells) were utilized, establishing the first OOC model that contains both fetal and maternal cells. Cell loading concentration into each chamber mimicked those of in utero cell ratios of the fetal membrane tissue. The microfluidic channel array prevented cells from flowing into the neighboring compartments during initial cell loading, allowing localized drug treatment of each cell layer, and allow taking supernatant from each layer independently for local biochemical analysis. At the same time, these channels allow biochemicals to diffuse between the layers, and also permit cell migration and transition. Taken together, this structure is similar to having distinct cell layers, as seen in the membrane-decidua fetal membrane-decidua (F-M) interface. Data using this model over a 5-7 day culture period was able to demonstrate ability to create F-M uterine infections and the model's capability in measuring the extent of inflammation at each layer when infection or OS occurs at either the fetal or maternal side. This shows that an infection-induced pathological state of F-M was successfully established in the OOC model.

The same device structure can also be utilized to create an OOC model of the placenta-decidua interface. This model is composed of four rectangular culture compartments interconnected through arrays of microfluidic channels. These chambers represent the maternal decidua basalis, placental syncytiotrophoblast, cytotrophoblast, and human umbilical vessel endothelial cell (HUVECs) layers. The layout and dimensions of the four compartments are designed to create a uniform layout for cell culture, and to fit within a well of a 6-well culture plate. Here, the array of 24 microfluidic channels (5 µm height, 30 µm width, and 600 µm length) function similar as the OOC models described above, allowing localized cell loading and culture as well as localized biochemical analysis, while still allowing cell migration and biochemical diffusion between compartments. Entactin-collagen IV-laminin (E-C-L, Millipore) solution was diluted in a sterile serum-free medium for each cell line up to a final concentration of 10 µg/mL. Both sides of the membrane was coated with E-C-L solution, prior to use. Cell loading concentration into each chamber mimic those of in utero cell ratios of the placenta and umbilical cord. HUVEC and trophoblasts represent endothelium and epithelium of the interface, and trophoblast provide barrier functions as previously reported. This setup is similar to having distinct cell layers with semipermeable cell barriers, as seen in the human placenta and some advanced OOC models reported previously. Each rectangular culture compartment have inlet/outlets to load cells, apply culture media and stimulants, take out effluent for biochemical assays, and to conduct end-point immunofluorescent staining of the cells in the chip. To simplify the device operation without the need for tubing or syringe pumps, a media/effluent reservoir array block was placed on top of the main placenta-decidua interface-OOC (Pi-OOC) so that all operations could be conducted utilizing pipetting-based cell/reagent handling. This mode of pump-less operation is what allows 30-60 devices to be tested in parallel in one experimental run due to its simplicity in operation, something that is not possible if the device must operate with complex tubing connections and syringe pumps. For the OOCs, Type IV collagen matrigel was loaded into the microchannels. Cells were then loaded into each compartment. Next, the culture media reservoir block was placed on top of the OOC device and bonded together (after plasma treatment of the reservoir layer to enhance bonding). The media height differences and microfluidic channel dimensions/numbers can be adjusted to control the diffusion time between the compartments as needed.

In another variation of the co-culture model, a cervix on a chip OOC model was designed. Intrauterine infection and/or inflammation account for almost 40% of preterm births. Ascending vaginal infection is hypothesized to be the most common pathway of intrauterine infection. This model accommodates cells and tissues that may mimic the physiologic conditions as well as ascending vaginal-cervical infection and thus bridge the gap between animal models and human-based clinical trials.

The OOC models described above can be integrated in various combinations to mimic the organ system as a whole. For example, it is can be necessary to study both the placenta and fetal membranes separately as well as together due to their proximity in utero, and to also gain an understanding of the F-M interface crosstalk during statin treatment. Based on this, an eight-compartment multi-organ feto-maternal Interface OOC (Pi-FMi-OOC) design, composed of four rectangle cell culture chambers for placental cells and four elliptical cell culture chambers for fetal membrane-derived cells, all interconnected through arrays of microfluidic channels, was designed. Here, the array has 24 microfluidic channels, each having a dimension of 30 μm width, 5 μm height, and 600 μm length. This integrated OOC model contain physiologically relevant cell layers as identified in the two individual F-M interface models described above. The placenta and fetal membranes are connected through distinct decidua layers, the basalis and parietalis, mimicking the vascular junction in utero that delivers drug and other nutrients to both F-M interfaces. A media/effluent reservoir array block can be placed on top of the device to facilitate drug treatment, effluent collection, and cell collection at different time points.

For each of the OOC model described above, both healthy state and disease state can be created. To create a disease state, for example that of infection, molecules such as cigarette smoke extract that can cause oxidative stress or lipopolysaccharide (LPS) that mimics bacterial infection, can be applied to any of the cellular layer. This will create a disease state of the OOC models, functioning as a model of preterm birth.

Working Examples

Reference will now be made to more specific embodiments of the present disclosure. However, it should be noted that the disclosure below is for illustrative purposes only and is not intended to limit the scope of the claimed subject matter in any way.

This study protocol was approved by the institutional review board at The University of Texas Medical Branch (UTMB) at Galveston, TX, as an exempt protocol for using discarded placenta after standard term Cesarean deliveries (UTMB Project 69693). No subject recruitment or consent was required for this study. The AM-OOCs were developed and microfabricated at Texas A&M University (College Station, TX, USA), and cell-based studies were conducted at UTMB.

Clinical Samples and Cell Culture

AEC Culture. Primary AECs and AMCs were isolated from amnion membranes obtained from fetal membranes from term, not-in-labor, and Cesarean deliveries. Approximately 10 g of amnion membrane, peeled from the chorion layer, was dispersed by successive treatments with 0.125% collagenase and 1.2% trypsin. All cell culture reagents were purchased from MilliporeSigma (Burlington, MA, USA). Briefly, the dispersed cells were plated in a 1:1 mixture of Ham's F12-DMEM; supplemented with 10% heat-inactivated fetal bovine serum, 10 ng/ml epidermal growth factor, 2 mM L-glutamine, 100 U/ml penicillin G, and 100 mg/ml streptomycin at a density of 3-5 million cells per T75 flask; and incubated at 37° C. with 5% $CO_2$ until 80-90% confluency was achieved.

AMC Culture. AMCs were isolated from fetal membranes. Primary AMCs were isolated from the placental membranes of women experiencing normal parturition at term (i.e., not in labor) and undergoing a repeat elective Cesarean section. Reflected amnion (~10 g) was peeled from the chorion layer and rinsed 3 or 4 times in sterile HBSS (21-021-CV; Corning, Corning, NY, USA) to remove blood debris. The sample was then incubated with 0.05% trypsin-EDTA (25-053-CI; Corning) for 1 h at 37° C. (water bath) to disperse the cells and remove the epithelial cell layer. The membrane pieces were then washed 3 or 4 times using cold HBSS to inactivate the enzyme. The washed membrane was transferred into a second digestion buffer containing Eagle's minimum essential medium (10-010-CV; Corning), 1 mg/ml collagenase type IV, and 25 mg/ml DNase I and incubated in a rotator at 37° C. for 1 h. The digested membrane solution was neutralized using complete DMEM-F12 medium (10-092-CV; Corning), filtered using a 70-mm cell strainer, and centrifuged at 3000 rpm for 10 min. The cell pellet was resuspended in complete DMEM-F12 medium supplemented with 5% heat-inactivated fetal bovine serum (35-010-CV; Corning), 100 U/ml penicillin G, and 100 mg/ml streptomycin (30-001-CI; Corning). The resuspended cells were subsequently seeded at a density of 3-5 million cells per T75 and incubated at 37° C. with 5% $CO_2$ until 80-90% confluency was achieved.

Microfluidic AM-OOC Design. The AM-OCC platform was fabricated in polydimethyl siloxane (PDMS) using a 2-step photolithography and soft lithography technique. To create the master mold (FIG. 1C), 2 layers of photosensitive epoxy (SU-8; MicroChem, Westborough, MA, USA) with different thicknesses were sequentially patterned on a 3-in diameter silicon substrate. The first layer forming the 5-mm-deep microchannels was obtained by spin coating SU-8 3005 at 4000 rpm and soft baking at 95° C. for 4 min. It was then exposed to UV light through a photomask, followed by a postexposure bake at 95° C. for another 4 min. The second layer forming the cell culture chambers was 500 mm thick and patterned by spin coating SU-8 3050 at 1000 rpm, soft baked first at 65° C. for 24 h and then at 95° C. for 40 min, exposed to UV through a second photomask, and then postexposure baked in 2 steps, first at 65° C. for 5 min and then at 95° C. for 15 min. The master mold was then coated with (tridecafluoro-1,1,2,2-tetrahydro octyl) trichlorosilane (United Chemical Technologies, Bristol, PA, USA) to facilitate PDMS release from the master mold after replication.

PDMS devices were replicated from the master mold by pouring PDMS prepolymer (10:1 mixture, Sylgard 184; DowDuPont, Midland, MI, USA) on the mold, followed by curing at 85° C. for 45-60 min. The reservoirs to hold culture medium were punched out using a 5-mm diameter punch bit (Syneo, Angleton, TX, USA) mounted on a drill press. To improve the bonding of PDMS devices onto glass substrates and to make the device hydrophilic for easy cell and culture medium loading, the PDMS devices were treated with oxygen plasma (Harrick Plasma, Ithaca, NY, USA) for 90 s, followed by bonding onto glass substrates. The PDMS culture devices were then immersed in deionized water. For sterilization, an autoclave was used to sterilize the PDMS culture devices at 121° C. for 30 min.

Microfluidic AM-OOC Device Preparation for Matrigel Filling of Microchannels

Before using the AM-OOC, devices were washed 3 times with PBS, coated with Matrigel (Corning Matrigel Basement Membrane Matrix, DEV-free; 1:50 in PBS), and incubated at 37° C. with 5% $CO_2$ overnight. Diluted type IV basement membrane Matrigel was used to coat the microchannels connecting the outer and inner culture chambers, which mimics the amnion basement membrane in vivo. Through this process a thin layer of Matrigel is left in the outer and inner chamber after microchannels are filled, where this contact with basement membrane mimics amnion cell growth in utero.

Masson Trichrome Staining for Matrigel Imaging

Before and after AM-OOC experiments, devices were stained with Masson trichrome stain to image type IV collagen inside the microchannels. To show that Matrigel loading was working, devices were rinsed with PBS and fixed at room temperature with 4% paraformaldehyde for 20 min. The devices were then stained with Biebrich scarlet-acid fuchsin for 10 min and then rinsed with water 3 times. This process stained all the cells and collagen red. Next, phosphomolybdic-phosphotungstic acid was applied for 15 min, which removed the red stain from the collagen. Aniline blue solution was then added for 10 min to stain the collagen blue. Once the device was stained, it was rinsed 3 times with water and imaged. This procedure was additionally carried out on some devices after 48 h of cell culture to monitor collagen degradation caused by cell migration.

Fluorescent Dye Perfusion Assay

To determine to what degree culture medium in the AM-OOC could diffuse from 1 culture chamber to the other, which corresponds to how much inflammatory mediators can propagate from 1 chamber to the other, a set of perfusion assay experiments were conducted. FITC dye was loaded into the inner or outer chambers, and microscopy images were taken over time (0-70 h). Fluorescence intensity was used to measure the degree of diffusion from the center chamber to the outer chamber, or vice versa. ImageJ software (National Institutes of Health, Bethesda, MD, USA) measured the intensity of FITC dye that perfused through the microchannels (with and without type IV collagen Matrigel) and into the opposite chamber over 70 h. Intensity values were normalized between replicates using the following formula: [(intensity at time point−intensity at time zero)÷intensity at time zero]×100.

Cell Seeding and Culture in the AM-OOC

Before using the AM-OOC, devices were washed 3 times with PBS and coated with Matrigel as previously described. The next day, devices were washed 3 times with complete DMEM-F12 medium before cell seeding. Primary cells were then trypsinized and stained with live cell dyes for green fluorescent protein (GFP) (for AEC; CellLight Histone 2B-GFP) or red fluorescent protein (RFP) (for AMC; CellLight Histone 2B-RFP) following the protocol provided by the company (10594 and 10595; Thermo Fisher Scientific, Waltham, MA, USA). Then, 120,000 AECs were loaded into the outer chamber, and 40,000 AMCs were loaded into the inner chamber of the AM-OOC. The AM-OOCs were incubated at 37° C. with 5% $CO_2$ for 24 h before localized treatment (see next section).

Cell Culture Treatments in the AM-OOC

To test the effect of OS on cellular transition in the amnion membrane, each AM-OOC was treated with one of the following for 48 h: 1) normal cell culture conditions (control DMEM-F12 medium); 2) OS conditions [induced by treating cells with cigarette smoke extract (CSE)] diluted 1:25 in AEC medium or diluted 1:75 in AMC medium; and 3) to verify the effect of OS, cells were cotreated with an OS inducer (CSE) and an antioxidant or stress signaler p38 MAPK inhibitor [N-acetyl-$_L$-cysteine (NAC, 15 mM, A7250; MilliporeSigma] (23, 29) and SB203580 (13 mM, S8307; MilliporeSigma) (23, 29), a p38 MAPK inhibitor and a known inducer of EMT.

To induce OS in fetal membrane cells, CSE was used. Cigarette smoke from a single commercial cigarette (unfiltered Camel; R.J. Reynolds Tobacco, Winston Salem, NC, USA) was bubbled into 25 ml of AEC or AMC medium. The stock CSE was sterilized using 0.25 mm Steriflip filter unit (MilliporeSigma) and diluted to 1:50 (AEC) or 1:75 (AMC) in cell specific medium before use. This modification was necessary to minimize any drastic effects of CSE in a microfluidic 3-dimensional (3D) culture system than in a much bigger 2D cell culture system.

Because of AMCs' exaggerated response to OS inducers, a different CSE concentration was used to induce OS in AMCs compared with AECs' treatment. Once cells reached 70-80% confluence, each AM-OOC was rinsed with sterile PBS, serum-starved for 1 h, treated with the respective conditions, and incubated at 37° C., 5% $CO_2$, and 95% air humidity for 48 h. After 48 h, bright field microscopy (Nikon Eclipse TS100 microscope, 310 magnification; Nikon, Tokyo, Japan) or confocal microscopy (Zeiss 880, 310 magnification; Carl Zeiss, Oberkochen, Germany) was performed to determine cell morphology, percentage of microchannels containing cells, and number of cells that migrated through the microchannels to the other side of the chamber for each treatment.

Immunocytochemical Localization of Intermediate Filaments Cytokeratin and Vimentin Cell Staining. AEC and AMC immunocytochemical staining for vimentin (3.7 ml/ml; ab92547; Abcam, Cambridge, MA, USA) and cytokeratin-18 (CK-18; 1 ml/ml; ab668; Abcam) were performed after 48 h. Manufacturer's instructions were used to calculate staining dilutions to ensure uniform staining. After 48 h, cells were fixed with 4% paraformaldehyde, permeabilized with 0.5% Triton X, and blocked with 3% bovine serum albumin in PBS prior to incubation with primary antibodies overnight at 4° C. After washing with PBS, the AM-OOCs were incubated with Alexa Fluor 488-, 594-, and 647-conjugated secondary antibodies (Thermo Fisher Scientific) and diluted 1:2000 in 3% bovine serum albumin for 2 h in the dark. The AM-OOCs were washed with PBS, treated with NucBlue Live ReadyProbes Reagent (Thermo Fisher Scientific), and imaged as previously described.

Image analysis. Three random regions of interest per AM-OOC were used to determine red (CK-18) and green (vimentin) fluorescence intensity. Uniform laser settings, brightness, contrast, and collection settings were used for all images collected. Images were not modified (brightness, contrast, and smoothing) for intensity analysis. ImageJ software was used to measure vimentin and CK-18 staining intensity from 2 focal plans of 3 different regions per treatment condition at each time point. Image analysis was conducted in triplicate for all cell experiments.

Milliplex Luminex Assays for Inflammatory Cytokine Markers

Supernatant were manually collected from the reservoirs of both chambers after 48 h of treatment. Milliplex assays were performed with the cytokine IL-8 and granulocyte-macrophage colony-stimulating factor (GM-CSF) antibody-coated beads (HCYTOMAG-60K; Merck, Darmstadt, Germany) as indicators of general inflammation in cell supernatant. Standard curves were developed with duplicate samples of known quantities of recombinant proteins that were provided by the manufacturer. Sample concentrations were determined by relating the absorbance values that were obtained to the standard curve by linear regression analysis.

Statistical Analyses

All experiments were conducted in triplicate and images analyzed using Prism 7 software (GraphPad Software, La Jolla, CA, USA). One-way ANOVA and independent samples Student's t test were used, and $P<0.05$ was considered significant.

AM-OOC Development

Figure 1B:
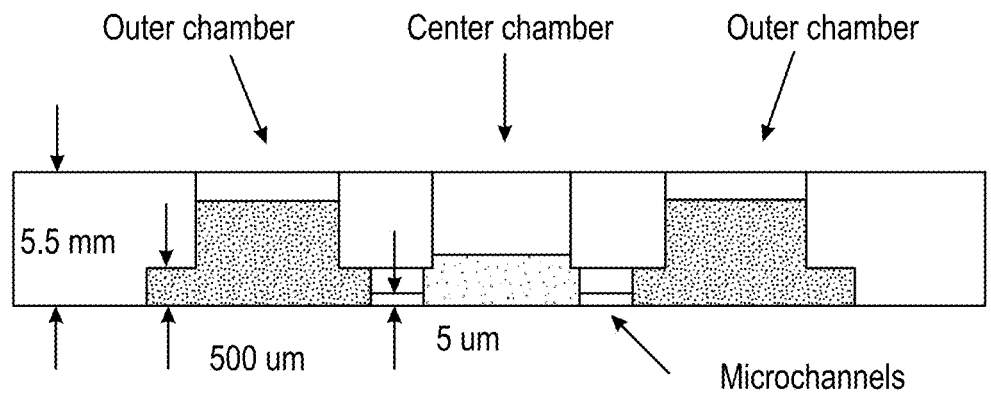
Figure 1C:
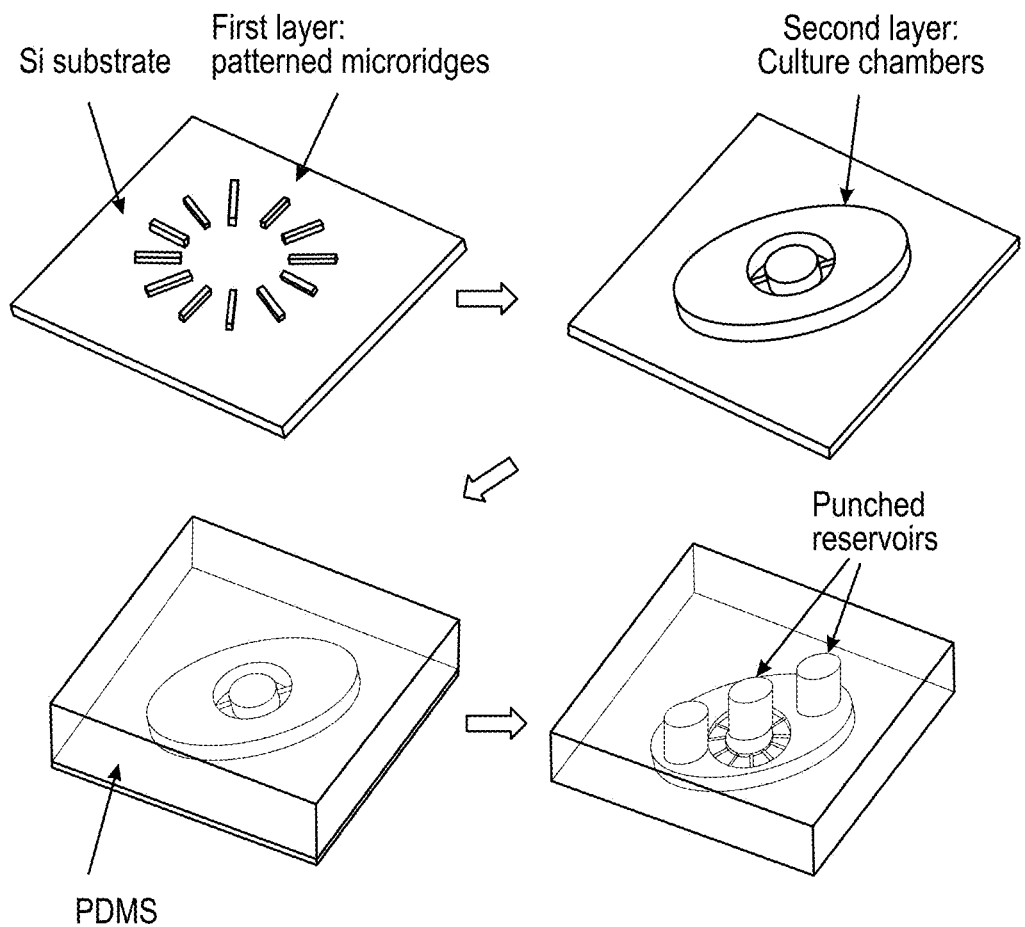
Figure 1D:
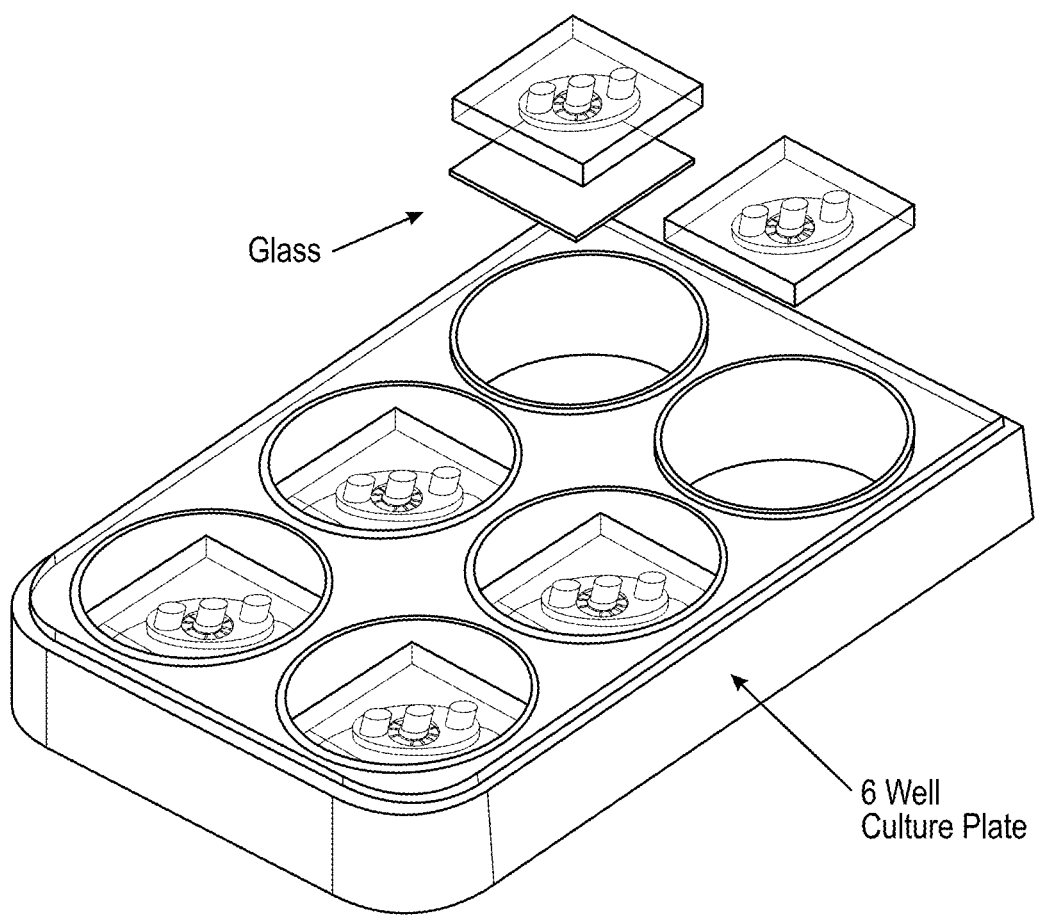

The AM-OOC device is composed of two circular chambers, one for AEC culture and one for AMC culture, connected through arrays of microfluidic channels (FIG. 1A). The center circular chamber is for AMC culture, and the outer ellipse-shaped chamber is for AEC culture. The outer and inner chambers measure 500 mm in height and are connected by 24 microfluidic channels (5 mm in height, 30 mm in width, 600 mm in length; FIG. 1B). Each device contained an outer chamber with two reservoirs and an inner chamber with one reservoir (FIG. 1C). Because of the device's small height, suspended cells initially loaded into each culture chamber remain in each chamber while still allowing cellular migration. In addition, in some cases, diluted type IV Matrigel was used to fill these microfluidic channels to mimic the amnion basement membrane, as further detailed below. When applying localized stimuli to only the AECs, the culture medium level of the center AMC culture chamber was maintained at a higher fill level compared with the outer AEC culture chamber, preventing any biochemicals and metabolites from AECs from diffusing into the AMC chamber because of the hydrodynamic pressure difference created by the different fluidic level. When applying localized stimuli to only the AMCs, the fluid height difference was reversed. Such hydrodynamic pressure difference-based localized coculture has been previously utilized for neuron-glia cell coculture. After sterilization, each device was placed in a conventional 6-well plate (FIG. 1D) and coated with type IV collagen Matrigel. Primary cuboidal AECs were loaded into the outer chamber, and primary AMCs were loaded into the inner chamber. Cells were cultured in good health over 2 d, each showing representative morphologies. The inner AMC culture chamber was filled with blue dye, and the outer AEC culture chamber was filled with red dye. Matrigel coating successfully produced collagen-filled microchannels (blue stain) to mimic amnion basement membrane, enabling isolation of the 2 different culture conditions while still allowing molecular communication as well as cell migration.

Fluidic Isolation Over Time Between the AMC and AEC Chambers in the AM-OOC

Figure 2A:
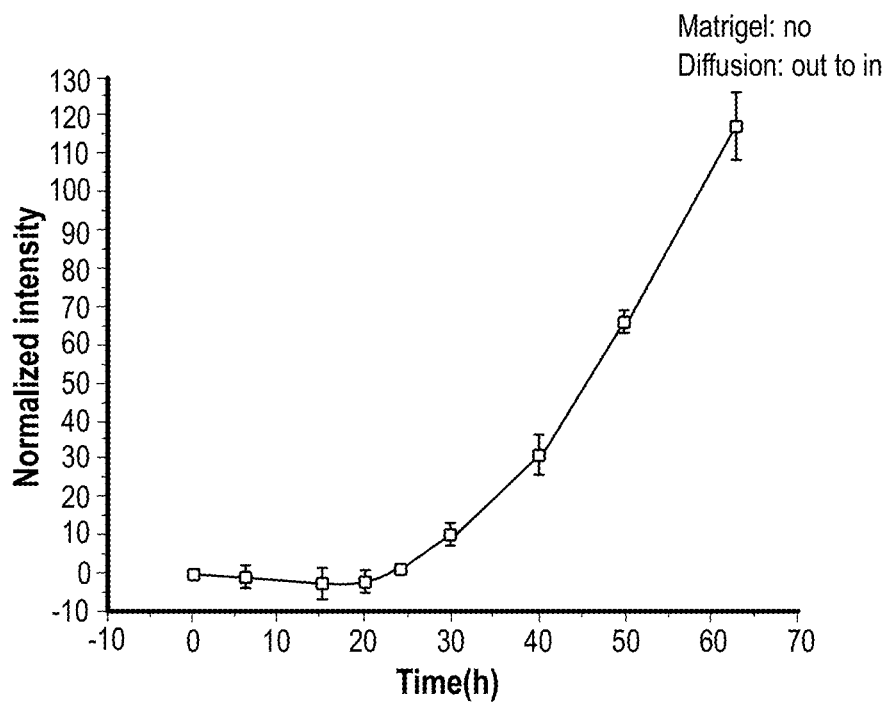
FIGS. 2A-2D illustrate fluid perfusion in the AM-OOC over time. Fluorescein isothiocyanate (FITC)-based perfusion assay showing fluidic isolation between the 2 culture chambers of the AM-OOC device over 60 h is shown.
Figure 2B:
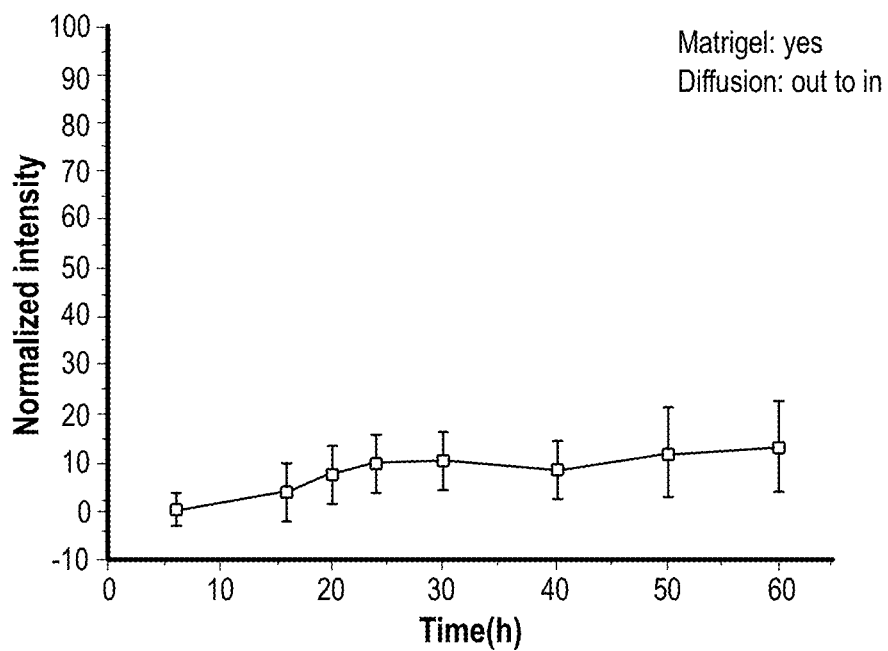
Figure 2C:
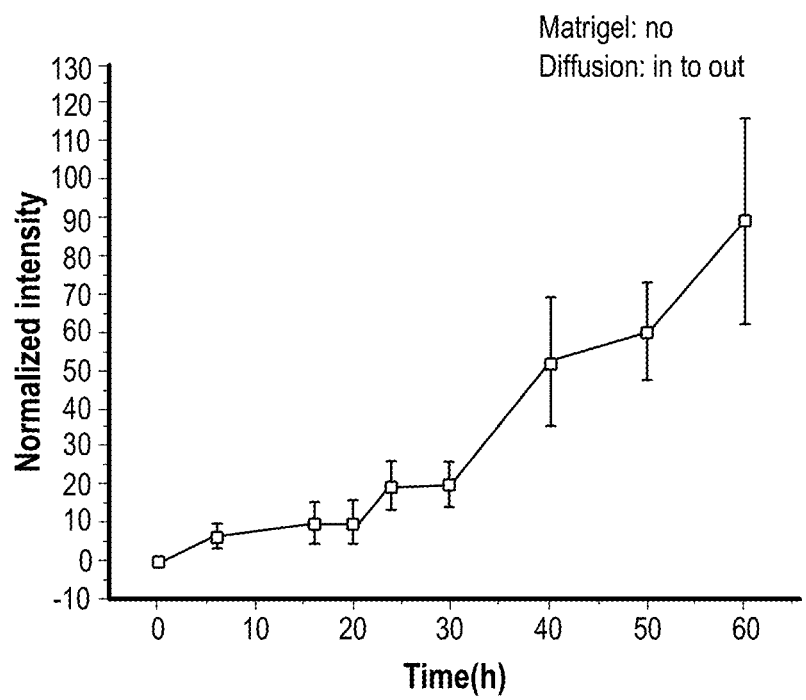
Figure 2D:
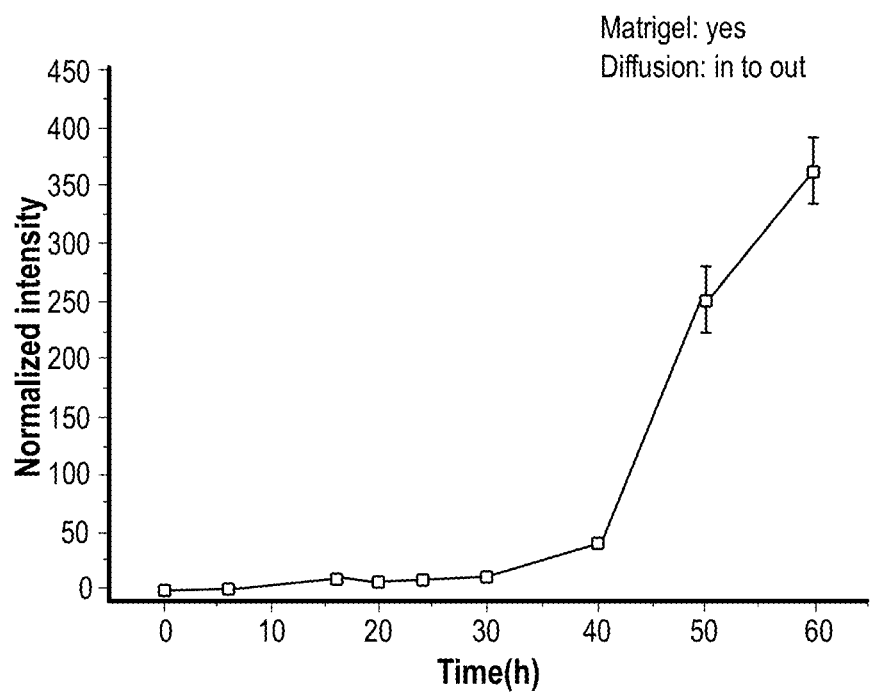
Figure 17A:
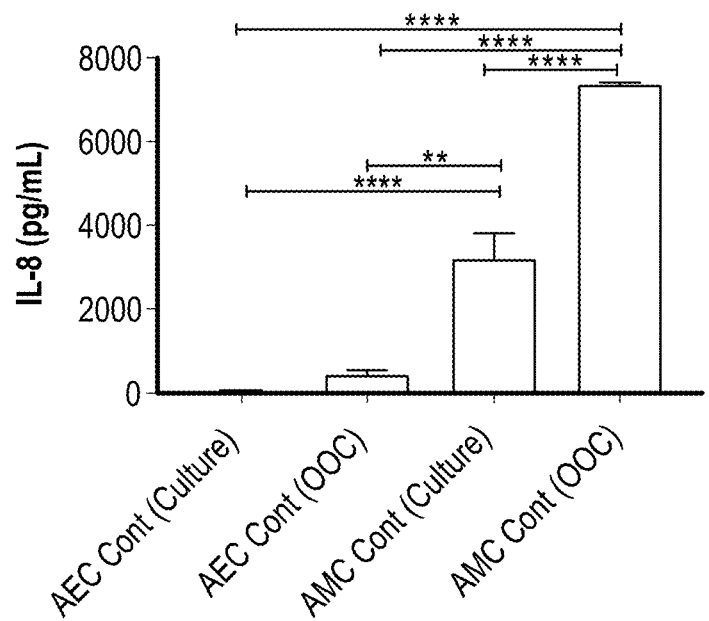
FIGS. 17A-17C illustrate production and propagation of proinflammatory mediators in the AMOOC monoculture system. Oxidative stress induced proinflammatory mediator production in AECs and AMCs in single cell culture and did not induce propagation of inflammatory mediators.
Figure 17B:
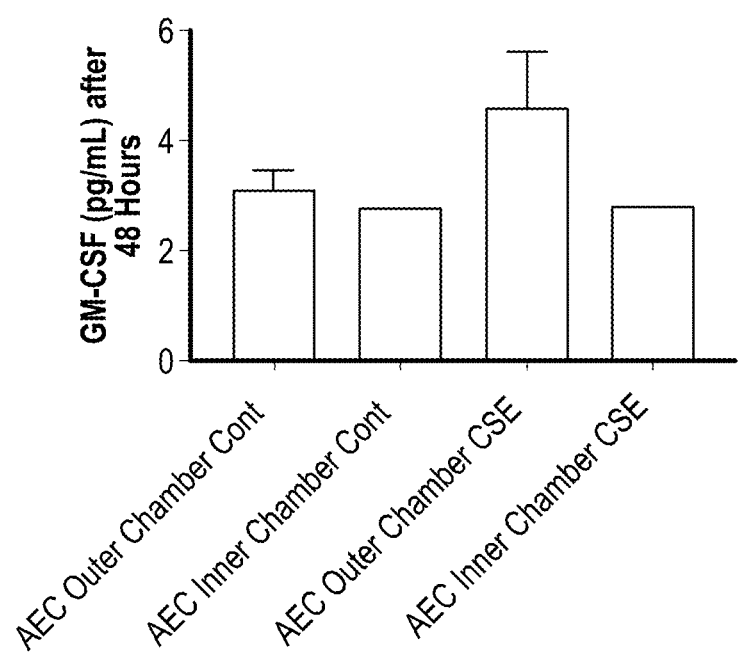
Figure 17C:
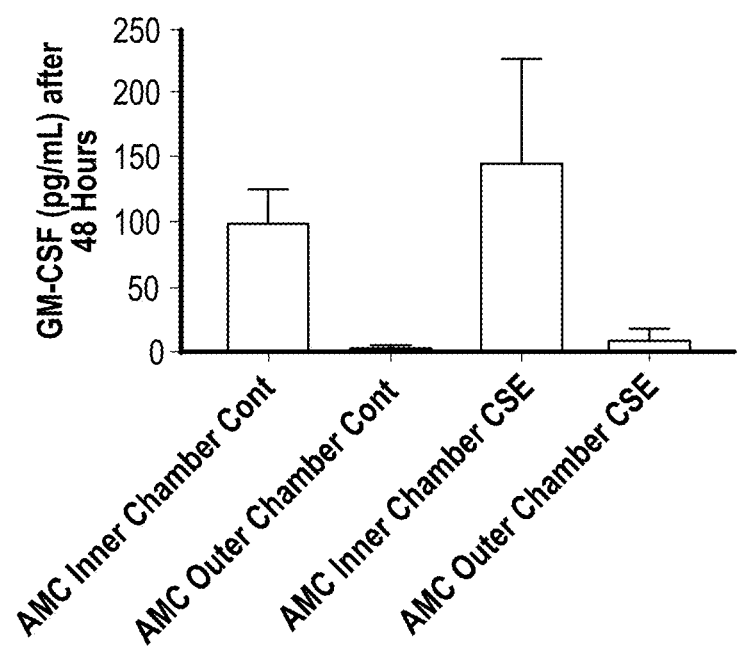

In the multicellular AM-OOC system, fluidic isolation between the two chambers is used to independently control and manipulate the two cell types and their microenvironments, while still allowing interactions between the two cell types. The efficiency to maintain fluidic separation between the two chambers was tested using a FITC-based perfusion assay in the AM-OOC by creating a minute fluidic level difference between the outer and inner chambers that resulted in hydrostatic pressure differences. FITC or PBS was loaded into either the outer or inner chamber, and fluorescence microscopy was used to monitor the rate of perfusion between the two chambers. When the inner chamber had a higher fluidic level than the outer chamber, it took more than 24 h for the FITC in the outer chamber to diffuse into the inner chamber, successfully demonstrating fluidic isolation between the two chambers (FIG. 2A). The use of type IV collagen-filled microfluidic channels extended this isolation time to 60 h (FIG. 2B). Similarly, fluid pressure from the outer to inner chamber counteracted some of the diffusion and allowed fluidic isolation for at least 20 h (FIG. 2C). The use of type IV collagen-filled microfluidic channels extended this fluidic isolation time to 40 h (FIG. 2D). Additionally, the difference in fluidic levels was also able to prevent proinflammatory cytokine propagation (GM-CSF) from diffusing from one chamber to the other chamber (FIGS. 17B-17C), further confirming successful fluid isolation between the 2 chambers.

Characteristics of Monoculture of AECs and AMCs in the AM-OOC

Amnion Cells Show Migratory and Transition Capacity. Monoculture of AECs (outer chamber) or AMCs (inner chamber) in the AM-OCC showed that cells can enter into the type IV collagen-filled microchannels, elongate, migrate through type IV collagen, and exit the microchannel within 48 h. Migrated cells either revert to their original epithelial shape or maintain their achieved mesenchymal morphology, clearly showing that direct imaging of cell migration through the collagen-filled microfluidic channel is possible in the developed AM-OOC.

Figure 3A:
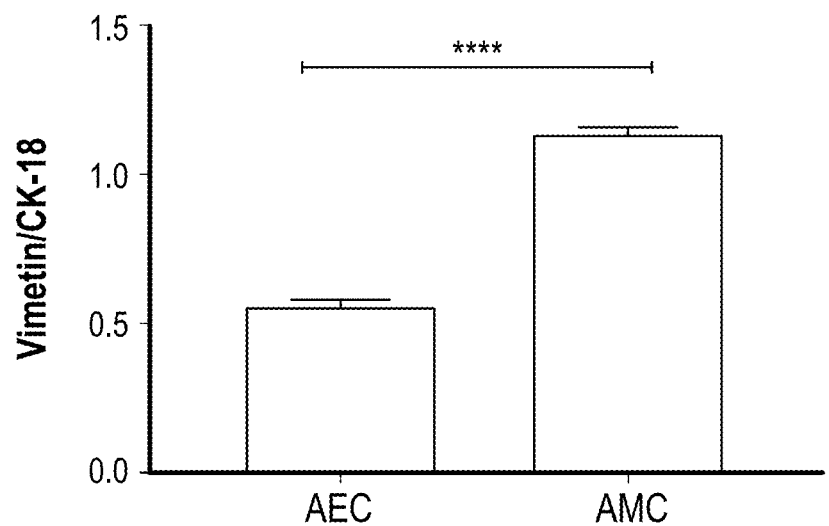
FIGS. 3A-3D illustrate AEC and AMC characteristics inside an AM-OOC device.
Figure 3B:
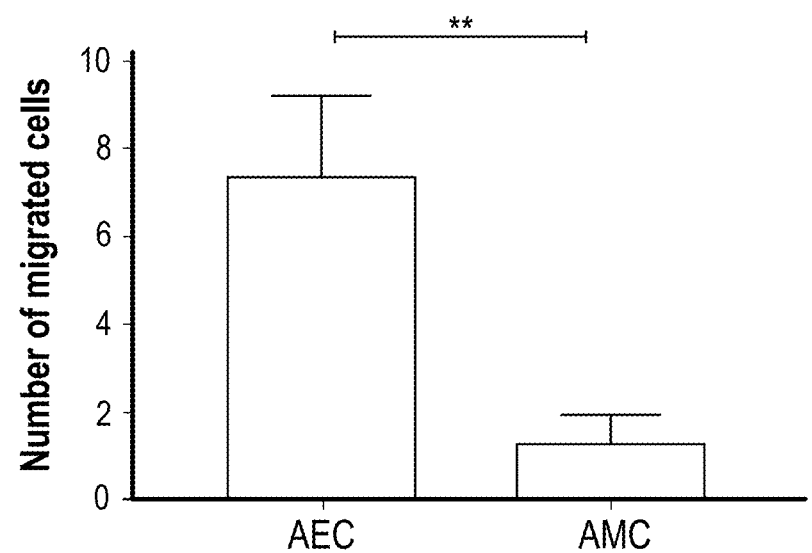

Amnion Intermediate Filament Expression and Migratory Potential. Results confirm that AECs innately express both epithelial and mesenchymal markers (i.e., CK-18, red; vimentin, green; low vimentin:CK-18 ratio; FIG. 3A), suggesting they are in a metastate or an in-between state of cellular transition. AMCs predominantly expressed mesenchymal marker vimentin as shown by the significantly higher vimentin:CK-18 ratio compared with AECs ($P<0.0001$; FIG. 3A). Furthermore, AECs in a metastate contained a significantly higher migratory potential ($P=0.0064$) than AMCs, likely because of the attainment of mesenchymal transition characteristics and metastate status (FIG. 3B).

OS Induces Changes in Amnion Intermediate Filament Expression and Migration

Increased OS at term has been shown to induce labor-associated changes, such as cellular senescence, matrix metallopeptidase 9 up-regulation, and increased proinflammatory cytokine production in fetal membrane cells, including AECs and AMCs. CSE, a potent and reliable OS inducer, has been shown to recreate the labor phenotype (OS experienced at term labor in amnion membranes) in vitro and to induce a static state of EMT in AECs. EMT contributes to sustained inflammation that promotes the labor-related cascade of events.

Figure 3C:
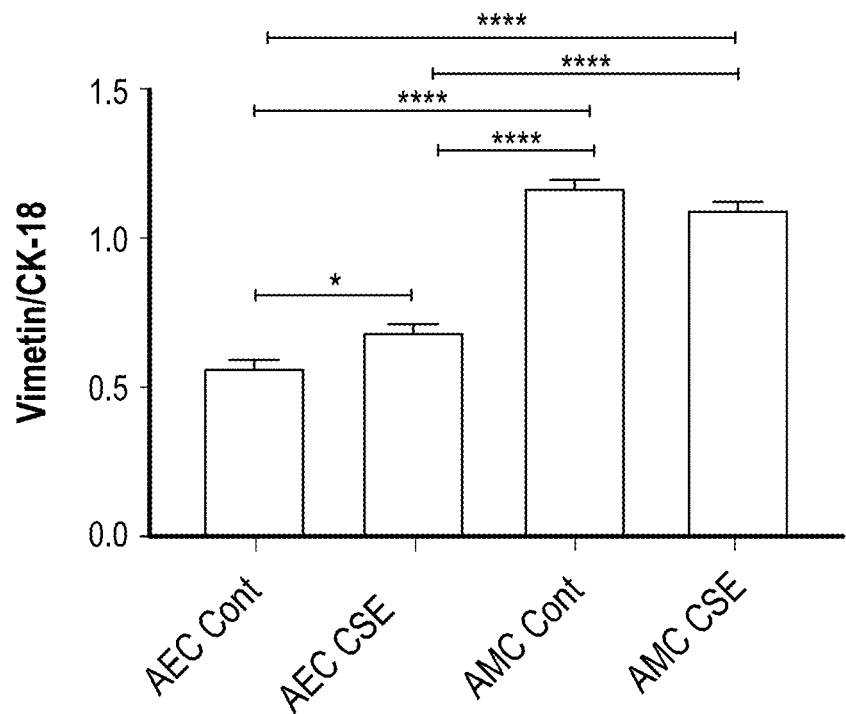
Figure 3D:
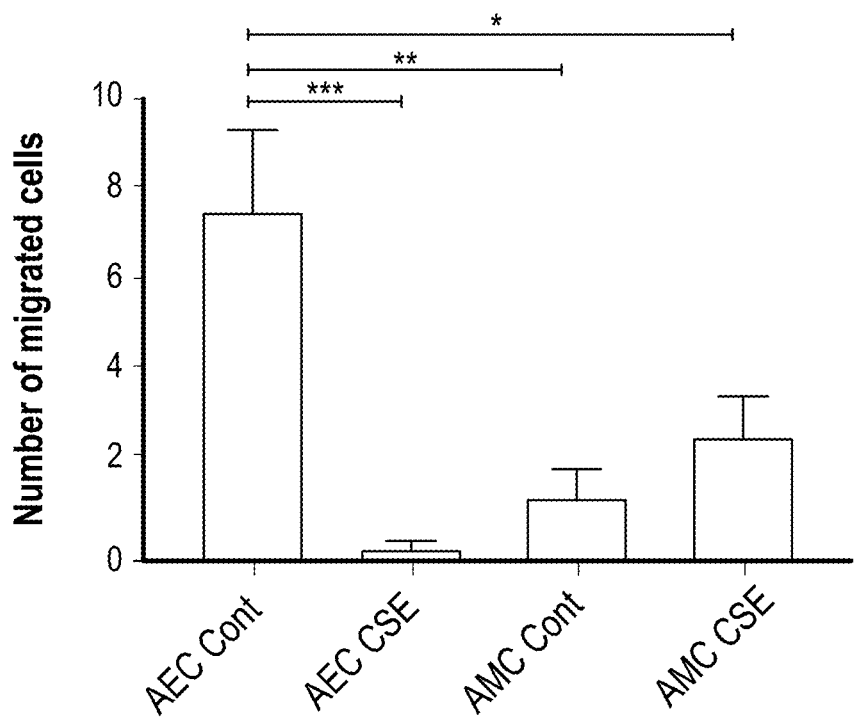

Data from this study indeed confirmed findings that CSE treatment for 48 h induced a fibroblastoid morphology in AECs and vimentin relocalization to the leading edge of migratory cells and significantly increased vimentin:CK-18 ratio (control: 0.56±0.02, CSE: 0.67±0.02; $P=0.02$) compared with AECs under standard cell culture conditions [vimentin (perinuclear)] and CK-18 (cytoplasmic; FIG. 3C). These changes are indicative of CSE inducing EMT in AECs while significantly decreasing their migratory potential ($P=0.0005$). Although mesenchymal characteristics are attained that should contribute to more cellular kinesis, the CSE-induced loss of migratory potential observed in this study is likely due to senescence of cells and independent of transition status. CSE treatment of AMCs resulted in maintenance of their mesenchymal phenotype (FIG. 3C) and increased level of migration compared with AECs (FIG. 3D).

Characteristics of Cellular Transition in AM-OOC Under Normal and OS Conditions

Figure 4A:
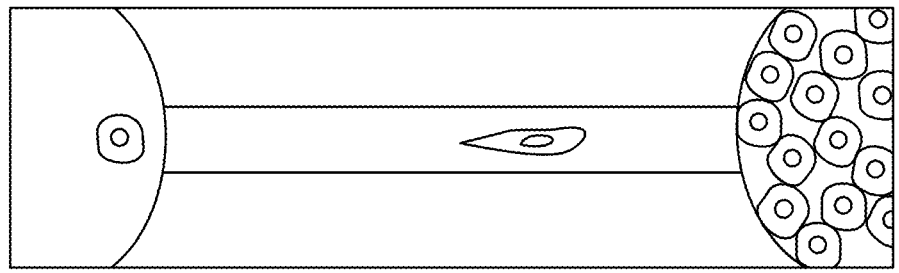
FIGS. 4A-4H illustrate OS's effect on cell migration and transition in monoculture. Confocal images measuring vimentin:CK-18 levels in AECs and AMCs during cell migration (n=3). Blue—DAPI, green—vimentin, and red—CK-18. Values are expressed as mean intensities±scanning electron microscopy (SEM).
Figure 4B:
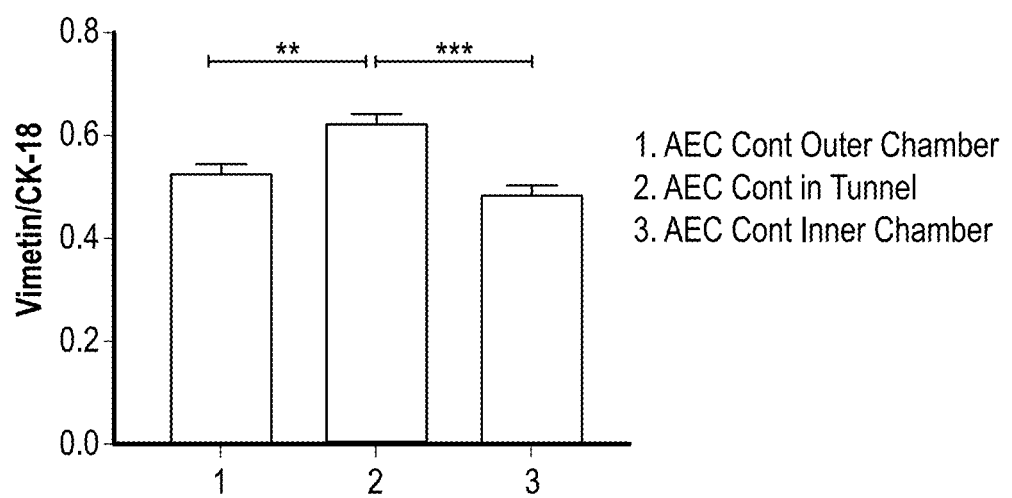

Innate Transition Properties of AECs. Confocal microscopy documented amnion cell morphology, intermediate filament expression, and cellular transitions to better understand how amnion cells migrate and degrade basement membrane collagen inside microchannels. Microscopy revealed that AECs under innate conditions express basal levels of vimentin:CK-18 (0.5±0.01), perinuclear vimentin, and an epithelial morphology. Migration of AECs was accompanied by a significant increase of vimentin:CK-18 ratio (0.62±0.02; P=0.0025), vimentin relocalization to the leading edge, and a fibroblastoid morphology, suggesting cellular transition (EMT). Once AECs completely migrated to the inner chamber, however, they reverted to basal expression of vimentin:CK-18 ratio (0.48±0.02; P=0.0009), perinuclear vimentin, and an epithelial morphology indicative of MET (FIG. 4A (schematic representation), FIG. 4B). Thus, the results show that AECs must undergo two cellular transitions, EMT to migrate and MET to exit, to completely migrate through the type IV collagen-filled microchannels. These transitions are similar to what has been reported in scratch assays that resembled membrane MF healing, in which migrating, and healing edges had mesenchymal and epithelial phenotypes, respectively.

Figure 4C:
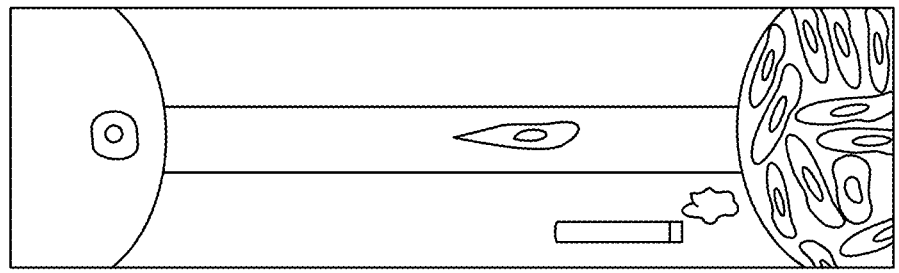
Figure 4D:
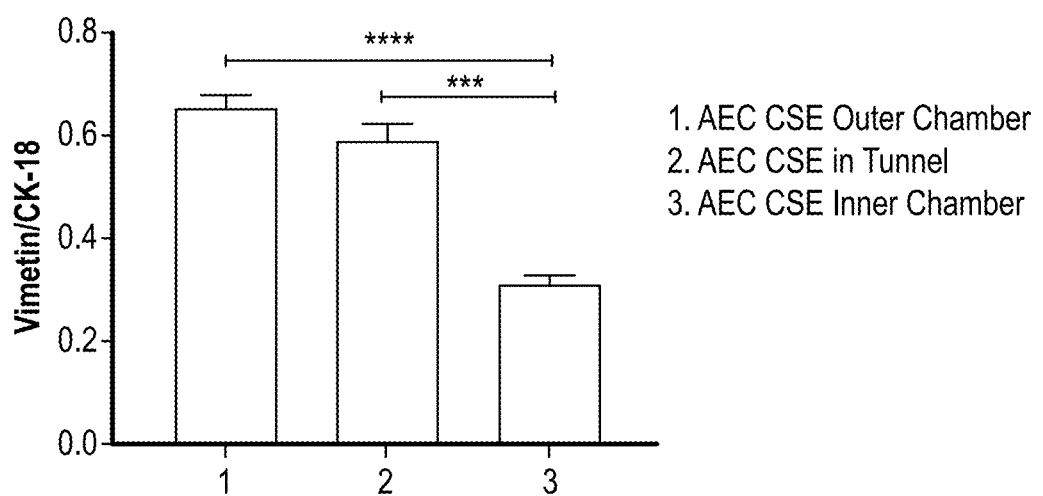

OS-Induced Static State of EMT in AECs. 48 h OS-treated AECs in the outer chamber expressed higher basal levels of vimentin:CK-18 compared with control AECs (FIG. 4B vs. FIG. 4D), indicative of a mesenchymal phenotype. Migrating AECs maintained their fibroblastoid characteristics while relocalizing vimentin to the leading edge; however, because of OS-induced senescence, most cells that underwent EMT were retained inside the microchannels, and the majority of them were unable to transition to an epithelial phenotype to exit, which is in line with findings that OS inhibits migration in AECs (control: 7.4±1.7 cells, CSE: 0.2±0.2 cells; P=0.0005; FIG. 3D). However, the few AECs that crossed the microchannels did undergo MET, inducing basal vimentin:CK-18 ratio (0.3±0.02; P=0.0004) levels and an epithelial morphology (FIG. 4C (schematic representation), FIG. 4D), suggesting the influential role of microenvironment in transitioning amnion membrane cells.

Figure 4E:
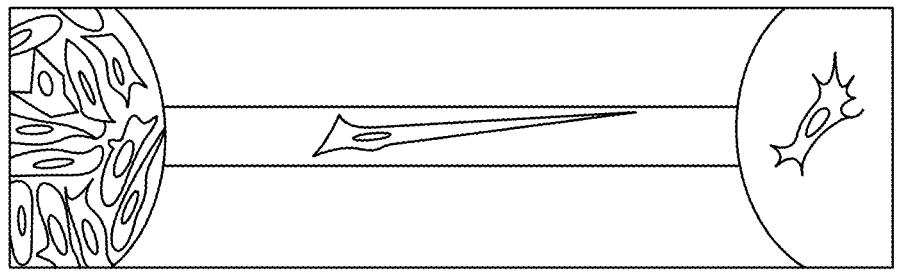
Figure 4F:
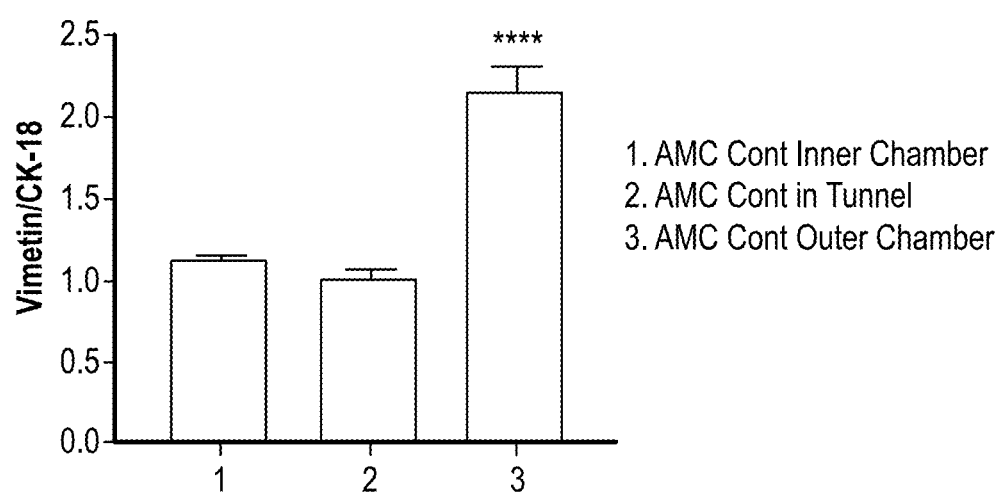
Figure 4G:
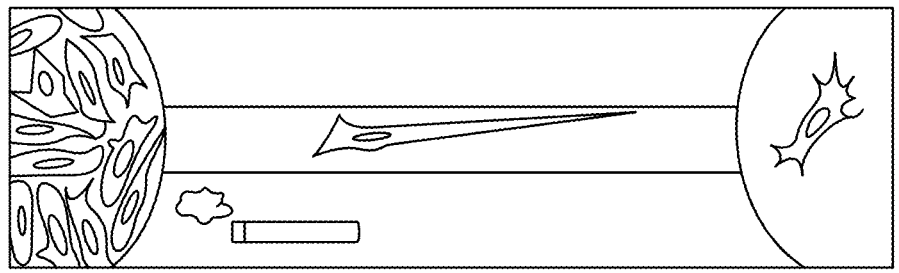
Figure 4H:
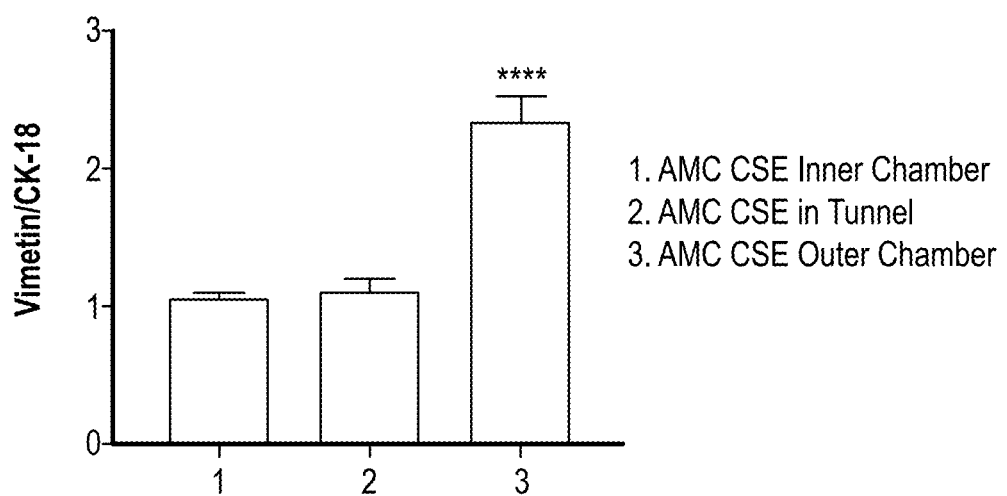

OS Does Not Change Innate Transition Properties of AMCs. AMCs in the inner chamber both under normal conditions and after OS exposure expressed relatively high levels of vimentin:CK-18 ratio (control AMC: 1.1±0.2, CSE AMC: 1.1±0.2; P=ns). Migrating AMCs maintained their vimentin:CK-18 ratio (control AMC: 1.0±0.03, CSE AMC: 1.1±0.09) while relocating vimentin to the leading edge. AMCs that migrated into the outer chamber had significantly higher vimentin:CK-18 ratio (control AMC: 2.1±0.14, CSE AMC: 2.4±0.2; migrating vs. emigrated AMCs: control: P<0.001, CSE: P<0.001) while also inducing native vimentin localization and morphology (FIG. 4E (schematic representation), FIG. 4F, FIG. 4G (schematic representation), and FIG. 4H). These data suggest that AMCs do not require cellular transitions (EMT to migrate and MET to exit) to migrate through microchannels, contrary to the behavior of AECs.

Characteristics of Cocultured AECs and AMCs in AM-OOC

To recreate the physiologic context of the amnion membrane components, AEC and AMCs were cocultured inside the AM-OOCs to study tissue dynamics. Crystal violet stain documented that both amnion cell populations were viable after 48 h. To determine the effect of coculture on cellular transitions and migration, live AECs were stained with a histone 2B-GFP and AMCs with a histone 2B-RFP to track them during and after migration. Each chamber was treated individually with control, CSE, or CSE with OS inhibitor NAC plus p38 MAPK functional inhibitor SB203580 (CSE+; Table 1). Both of these inhibitor compounds have been shown to reduce the deleterious effects of OS- and stress-associated signaling in amnion cells, which is why they were selected for the experiment.

TABLE 1

Summary of coculture treatments and abbreviation.

| Treatment | Outer chamber treatment | Inner chamber treatment | Abbreviation |
|---|---|---|---|
| 1 | Control | Control | Control/control |
| 2 | CSE | Control | CSE/control |
| 3 | Control | CSE | Control/CSE |
| 4 | CSE | CSE | CSE/CSE |
| 5 | CSE + NAC + SB | CSE + NAC + SB | CSE+/CSE+ |

CSE+, CSE with OS inhibitor NAC plus p38 MAPK functional inhibitor SB203580; SB, SB203580

Coculture Effect on Cellar Transitions. After examining what occurs during monoculture in either the outer or inner chamber of the AM-OOC, similar coculture experiments were performed under fluidic isolation conditions (fluidic isolation shown in FIGS. 2A-2D). Under normal coculture conditions, GFP-labeled AECs expressed epithelial morphology in the outer chamber, underwent EMT, migrated, and maintained their mesenchymal morphology to join the AMC population in the inside chamber (FIG. 5A (schematic representation)). Similarly, RFP-labeled AMCs migrated and underwent MET to an epithelial morphology while assembling into the AEC population (FIG. 5A (schematic representation)), emphasizing AECs' and AMCs' ability to transition under distinct environmental conditions.

Figure 5A:
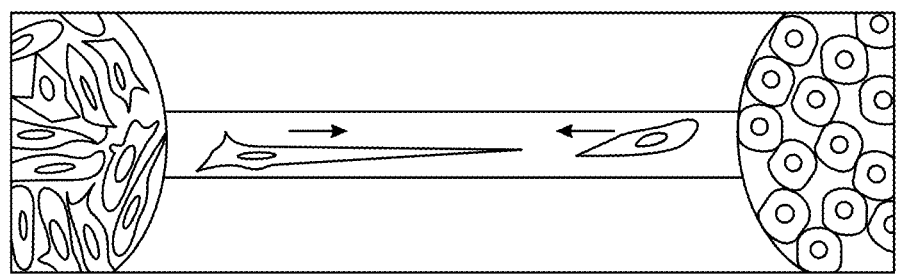
FIGS. 5A-5C illustrate OS' effect on migration and transition in AEC-AMC coculture. Confocal imaging of coculture experiments revealed that both cell types can migrate, transition, and integrate themselves into the emigrated environment (n=3). Confocal images showed native AECs and AMCs, transitioned, migrated, and integrated into the opposite population (n=3). GFP-AECs migrated through the type IV collagen tunnel, relocalized vimentin, and transitioned into a mesenchymal morphology indicative of EMT. Red fluorescent protein (RFP)-AMCs migrated through the type IV collagen tunnel, down-regulated vimentin, and transitioned into an epithelial morphology indicative of MET.
Figure 5B:
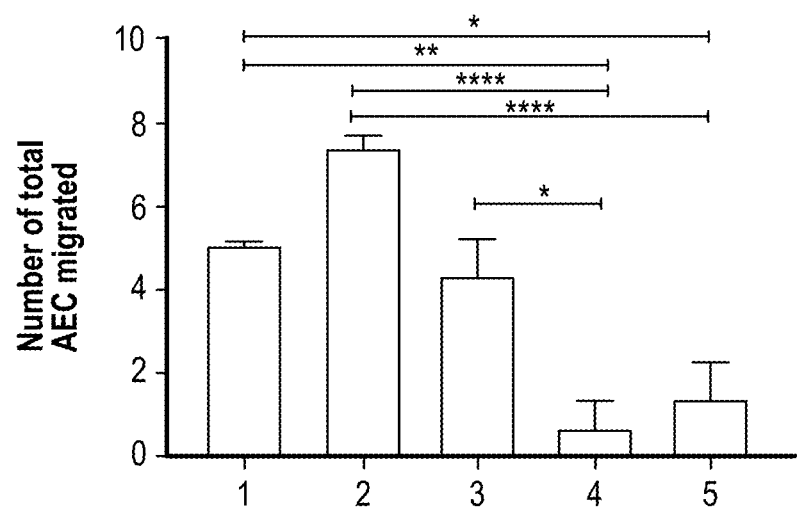
Figure 5C:
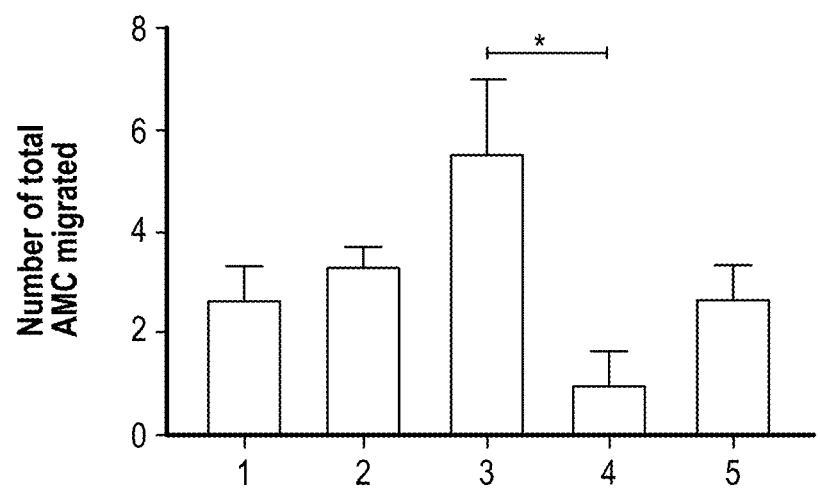

OS's Effect on Migration in Coculture. A bright field microscopy analysis showed that 48 h CSE treatment of AECs or AMCs in coculture induced migration more frequently than in respective controls (AEC control: 5.1±0.06, CSE: 7.3±0.3; AMC control: 3.3±0.3, CSE: 5.5±1.5). These results were different compared with monoculture experiments, highlighting the effect of coculture on cell migration. Localized CSE treatment of each chamber did not affect AECs' or AMCs' migration potential in their adjacent chambers, showing that localized CSE treatment in the AM-OOC is indeed possible. Interestingly, when CSE cotreatment was added to both chambers, cellular migration slowed, though not to a significant level. These effects were mildly prevented by cotreatment of CSE with NAC and SB203580 (CSE+; FIGS. 5B-5C) (AECs: CSE/CSE vs. CSE+/CSE+=2-fold higher) (AMC: CSE/CSE vs. CSE+/CSE+=2.5-fold higher), suggesting that OS and p38 MAPK downstream signaling could regulate AECs' and AMCs' migration.

Propagation of Inflammatory Mediators in AM-OOC Devices

Enzyme-linked immunosorbent assay (ELISA) for proinflammatory marker GM-CSF was evaluated 48 h after treatment to determine whether migratory cells induced inflammatory changes in the opposite chambers.

Figure 6A:
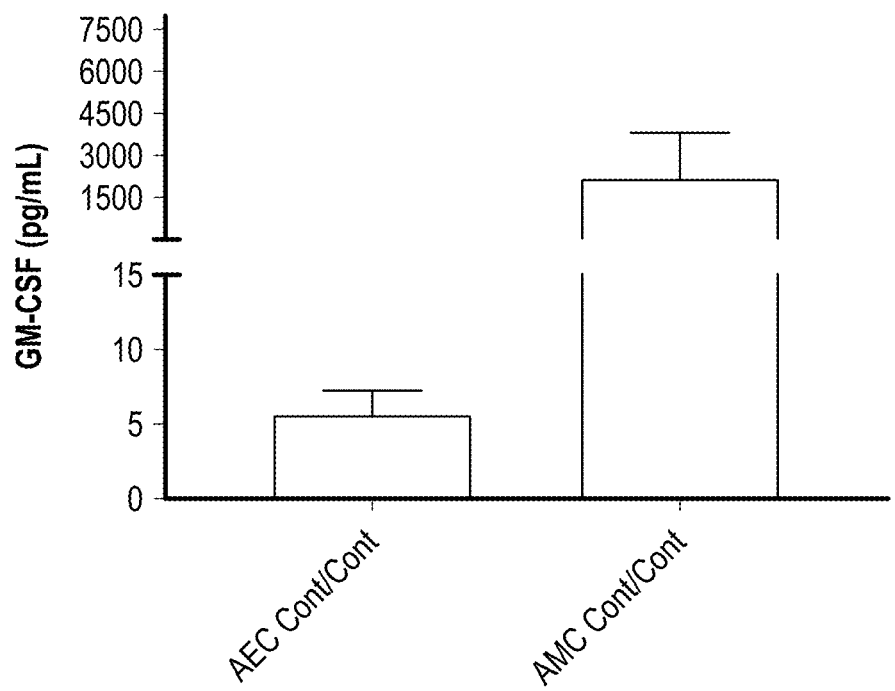
FIGS. 6A-C illustrates production and propagation of proinflammatory mediators in the AM-OOC coculture system. OS induced proinflammatory mediator production and propagation in amnion cells (n=3).
Figure 6B:
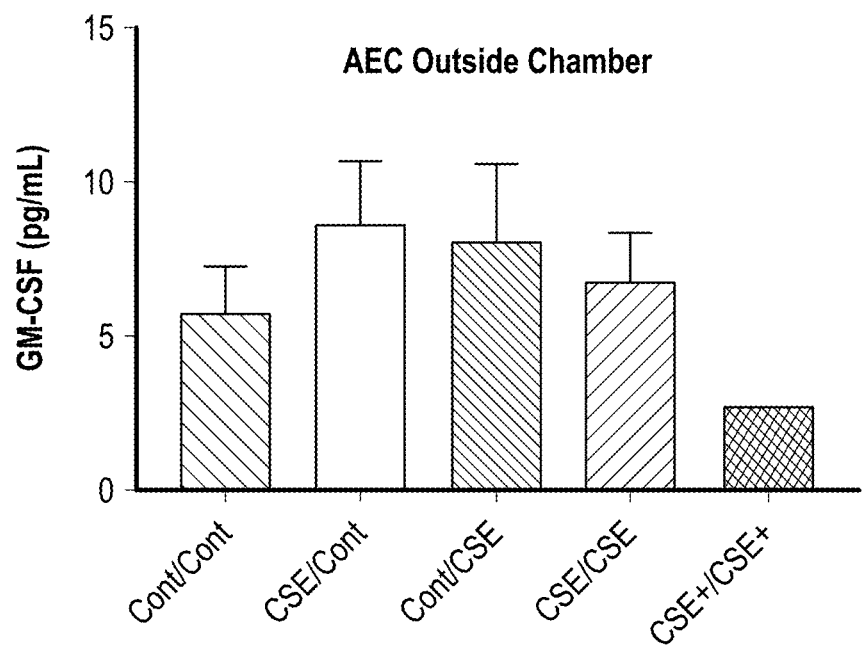
Figure 6C:
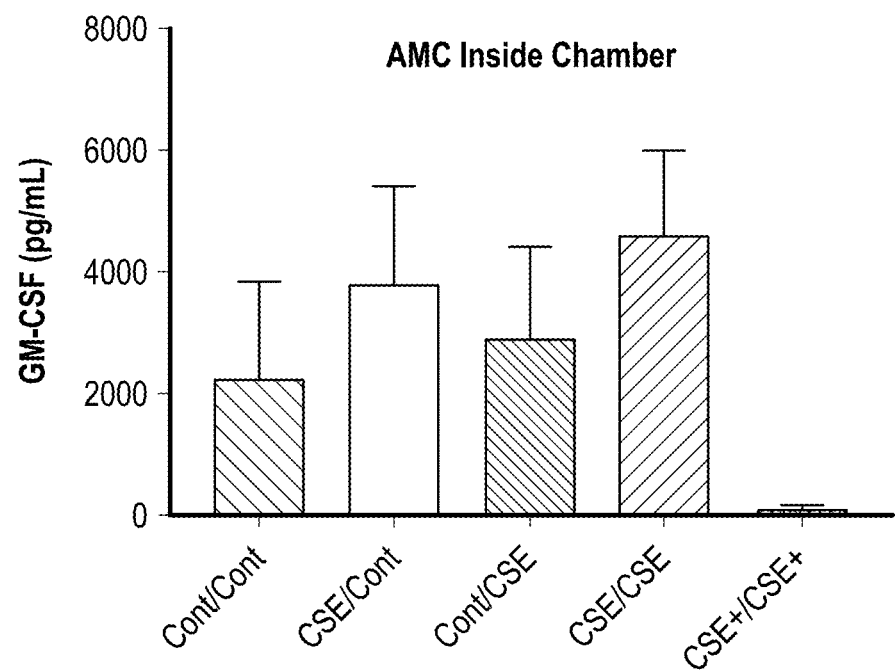
Figure 7A:
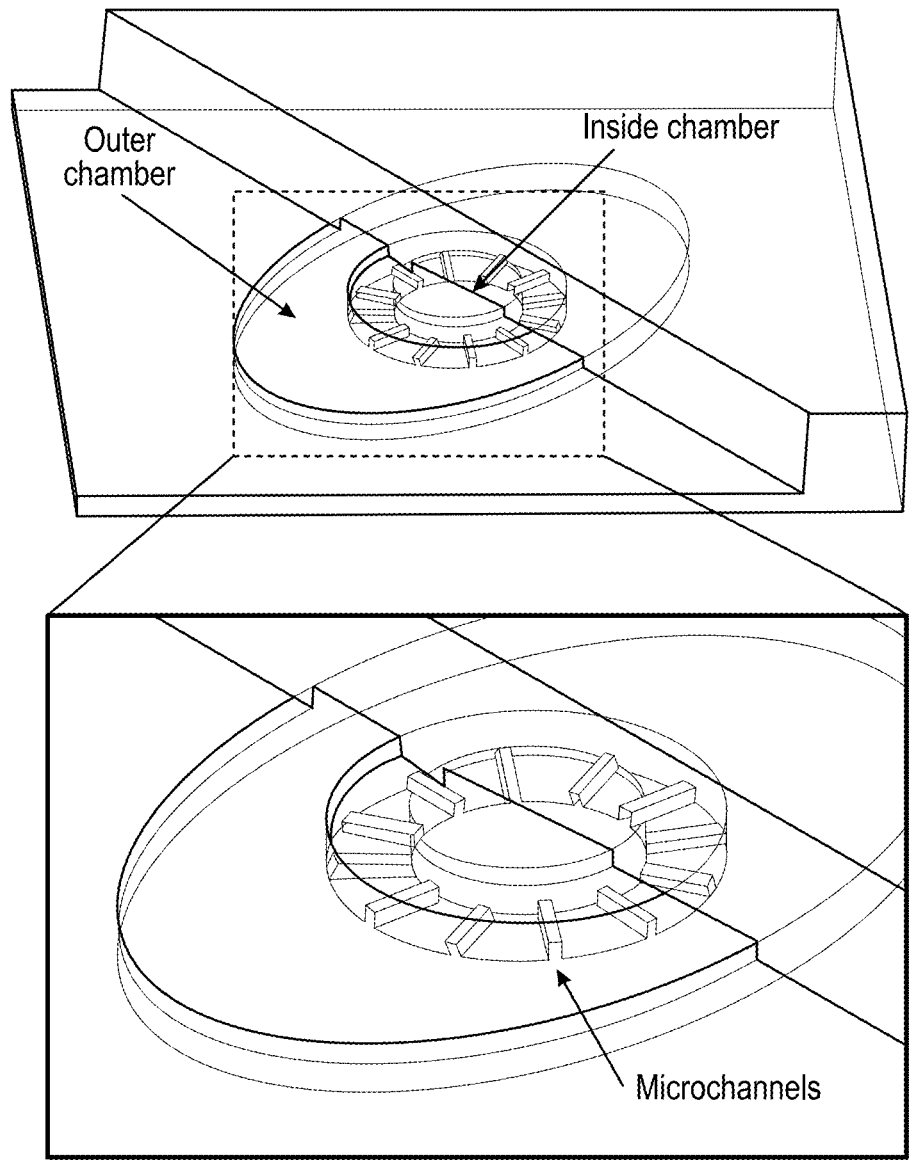
FIG. 7A illustrates a schematic illustration of an AM-OOC. 3D and cross-sectional view showing the physical isolation of AECs and AMCs connected by 24 microchannels filled with type IV collagen.
Figure 7B:
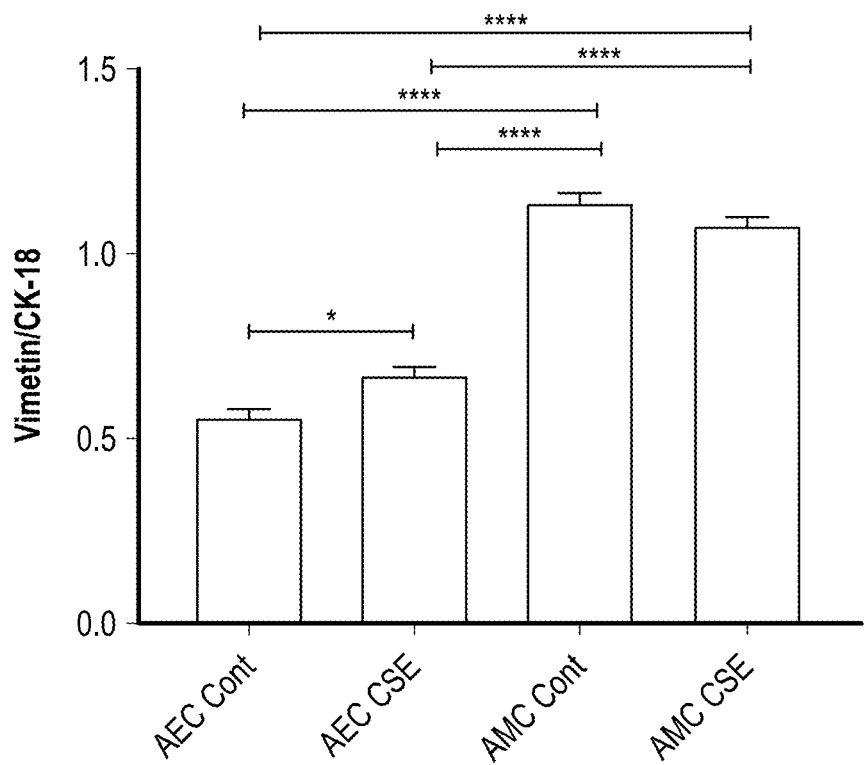
FIG. 7B illustrates analysis of confocal images show native and OS-induced (CSE) levels of vimentin and CK-18 expression in AECs and AMCs (AEC Control: 0.56±0.02, CSE: 0.67±0.02; AMC Control: 1.1±0.2, CSE: 1.1±0.2; n=3). CSE AECs had significantly higher vimentin/CK-18 levels compared to AEC controls (P=0.02), while AMC intermediate filament expression remained constant regardless of treatment. Confocal images were captured at 10×. Blue—DAPI, green—vimentin, and red—cytokeratin-18. Values are expressed as mean intensity±SEM.
Figure 7C:
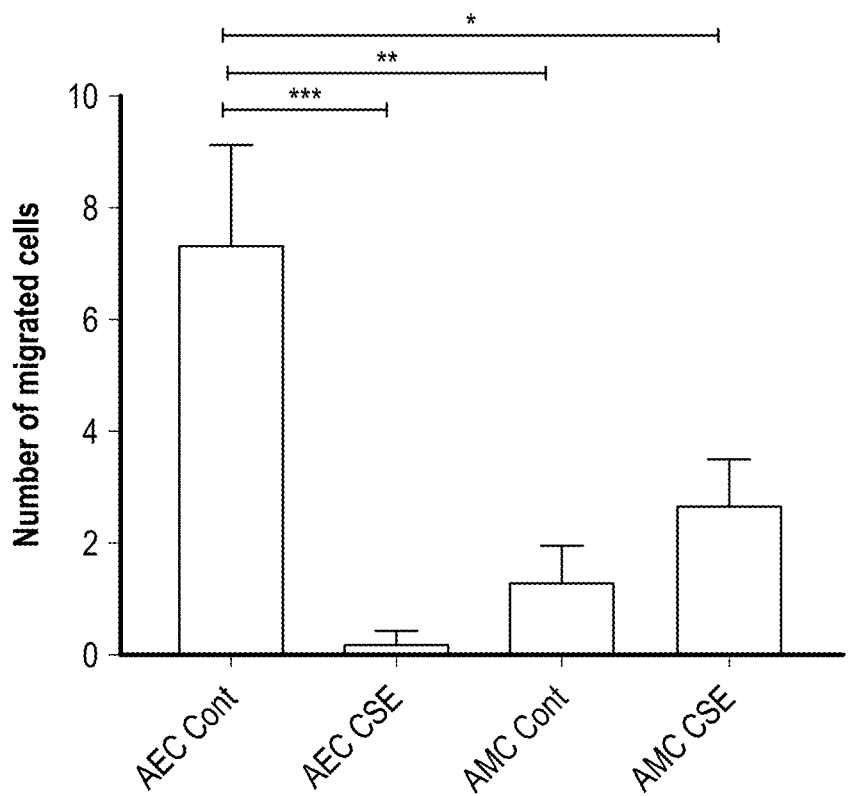
FIG. 7C illustrates analysis of bright field microscopy images shows CSE treatment inhibited migration of AECs compared to AEC controls (P=0.0005), while CSE treatment of AMCs stimulated migration. Control AECs contain the most migratory potential of all treatments and cell types.

Standard and OS-induced Inflammatory Mediator Expression. Consistent with the current literature, under coculture condition, AMCs naturally produced more proinflammatory cytokines compared with AECs, although this was not to a significant level (FIG. 6A). Furthermore, though not significant, CSE treatment of AECs and AMCs increased proinflammatory cytokines in both cell types [AEC: control: 5.7±1.5, CSE: 8.7±1.9] (FIG. 6B) [AMC: control: 2208±1629, CSE: 3835±1541] (FIG. 6C).

OS-Induced Inflammatory Mediator Propagation. The CSE treatment of one chamber was also shown to induce inflammatory mediator (GM-CSF) response in the opposite chamber [CSE AMCs' effect on control AECs, control/control: 5.7±1.5, control/CSE: 8.2±2.4] (FIG. 6B) [CSE AECs' effect on AMCs, control/control: 2208±1629, CSE/control: 3835±1541] (FIG. 6C), whereas CSE+ treatments lowered proinflammatory cytokine production compared with CSE alone in both cell types (FIGS. 6B-6C). Because fluid isolation was established (FIGS. 2A-2D and FIGS. 17A-17C) and CSE treatment did induce migratory changes in the cell population (FIGS. 5B-5C), without being bound by theory, it is postulated that inflammatory changes may be initiated from the migrated cells themselves or by supernatant leaking through cell induced tunnels in the collagen-filled microchannels.

Discussion

The AM-OOC developed and utilized in this study revealed amnion membrane cells' transition and migratory properties under interactive environmental conditions. The following was determined: 1) amnion membrane cells can transition and migrate through type IV collagen-filled microchannels; 2) OS induces a static (nonreversible) state of EMT, decelerates cell migration, and increases proinflammatory mediator production; 3) coculture experiments revealed that both cell types can migrate, transition, and integrate themselves into the emigrated environment; and 4) OS cotreatment propelled transition but inhibited migration of cells in cocultures and induced proinflammatory mediator production in the adjacent cell chamber. Inhibition of OS by antioxidants and functional inhibitors of stress signaler p38 MAPK reversing the changes further confirmed the influence and interaction between the AMCs and AECs.

Recreating the whole organ dynamics using OOCs is an idea that has been around for many years; however, only very recently has their usefulness been explored in the field of reproductive science. The female reproductive tract, placenta, and endometrium-on-chip have been developed and used to study multiple aspects of reproductive health, which have highlighted the importance of cell-cell and cell-blood interactions in vitro. Although development of a fetal membrane-on-chip has been postulated, no work has been reported. The present disclosure first focused on creating an in vitro culture model of the amnion membrane because it is a component of the fetal membrane. Another reason the present disclosure was initially focused on the amnion membrane, rather than the entire fetal membrane, is that it is only composed of two cell types, compared with the entire fetal membrane, which is composed of five cell types, from the fetal side as well as the maternal side. A model was previously developed that tested interactive features between fetomaternal interface cells, AECs, and maternal decidual cells. The current model was used to address the limitations of the previous model, including the following: its lack of an ECM, because cells are directly cultured on a synthetic nondegradable polymer membrane similar to those used in transwell inserts; its inability to locally stimulate only one cell type to properly study cell-cell interactions and causal relations in their effect; and the vertical organization of the device that prevents direct imaging of the culture chambers and migratory cells that move from one chamber to the other, to name a few. The AM-OOC developed overcomes these limitations by more accurately mimicking the amnion component of the fetal membrane, especially the existence of ECMs, while allowing different cellular components of the amnion to be independently controlled and stimulated and also allowing the direct monitoring of cellular migration through the ECMs using microscopy.

The amnion membrane provides the structural framework for the intrauterine cavity and contributes to pregnancy maintenance by bearing the tensile strain inflicted by the growing fetus. The highly elastic amnion layer of the fetal membranes maintains its integrity and function through constant remodeling mediated by cellular transitions and matrix rearrangements. AECs are more dynamic in their transitions because they line the inner surface of the intraamniotic cavity, whereas AMCs serve as reserve cells to fill gaps vacated by AECs in the ECM. Maintenance of membrane integrity during gestation and its mechanical and functional compromise at term involve both cellular and matrix components. ECM turnover by collagenolytic processes is well reported, and recent work has shed some insight into cellular-level changes. In that work, it was reported that OS's buildup at term causes stress signaler p38 MAPK-mediated senescence as well as EMT of AECs. Both of these conditions cause endogenous inflammatory responses associated with parturition. Histologic examination of senescent membranes revealed biologic MFs that are sites of remodeling. Although cell scratch assays can determine mechanisms of MFs' healing, those experiments lacked cellular interactions that may influence transitions and migrations. In addition, even though some level of evidence of cellular migration can be observed at distinct time points through microscopy, such migration could not be directly monitored. These limitations were addressed by the use of the AM-OOC model developed herein.

This study provides a novel approach to document sites of remodeling in vitro by visualization of cells migrating through collagen-filled microchannels. This very well may be facilitated by collagen degradation or even in its absence. This study did not specifically test this aspect; however, based on the nature of amnion cells, it is likely that they will produce type IV collagen-specific matrix metalloproteinases to propel themselves through these microchannels. During gestation, AECs and AMCs undergo cyclic cellular remodeling to heal gaps and MFs in the membranes, a mechanism required to maintain membrane homeostasis. Membrane remodeling at a cellular level is achieved by EMT of AECs and MET of AMCs, aided by redox radicals, growth factors (e.g., TGF-b), and endocrine mediators (e.g., progesterone). Cellular gaps are created when AECs are shed from the membrane because of cellular senescence, mechanical disruption caused by fetal and amniotic fluid shear stress, or both. These gaps lead to MFs' formation by shed AECs, which migrate through the ECM. This migration is aided by the mobility attained by AECs when they transition to AMCs. Endogenous progesterone recycles transitioned AMCs back to AECs with the production of nascent collagen to fill any degraded ECM components. These biologic processes maintain membrane integrity and cellular homeostasis during gestation. However, at term, an increased OS-induced static state of EMT increases inflammatory mesenchymal phenotype, leading to collagen degradation and mechanical failure of membranes.

These intrinsic in utero events were recreated in the AM-OOC and documented that treatment of adjacent cell populations in a controlled environment results in OS, inducing a static state of EMT and inflammation (FIGS. 3A-3D and FIGS. 4A-4H). In single cell culture, OS has also been previously shown to inhibit migration of AECs because of development of cellular senescence and independent of transition status. AEC single culture data from AM-OOC also reconfirmed these findings, suggesting that OS-treated microchannel cells are in a state of cellular senescence, which could contribute to migration inhibition. However, importantly, the model shows that this inhibition can be partially overcome when AECs are cocultured with AMCs that are maintained in a normal cell culture environment (FIGS. 5A-5C). Conversely, CSE cotreatment induced EMT in AECs but prevented migration and MET in AMCs. Thus, OS treatment induces a static state of EMT in the AM-OOC devices, similar to what is observed in term amnion membrane.

By recreating the full amnion component of the fetal membranes, this AM-OCC model provides a physiologic context that allows manipulation of multiple cell types and their microenvironments with high levels of accuracy. 3D cell culture models, such as amnion membrane explants, organoids, and transwell systems, offer an alternative approach to multilayer assessment of cell-cell and cell-collagen interactions in vitro. However, the ability to distinguish between individual cell signals and analyze how these signals propagate is lost because of the close proximity of different cell types in explants and organoids, or difficulties in manipulating each cell culture chamber in transwell systems. Additionally, most of these models are not compatible with direct imaging of cellular migration, cellular transition, and ECM degradation and thus cannot provide a detailed view or direct evidence of cell-cell interactions.

Traditionally, transwell culture systems are used to study fetal membrane signaling; however, their usefulness is limited because of the following reasons: 1) lack of physiologic separation of cell types in coculture; 2) controlling their respective microenvironments in co culture is not possible, and local application of stimuli to only one compartment is difficult; 3) direct monitoring of any collagen matrix degradation caused by cellular migration is not possible; 4) imaging of cellular migrations and transitions is limited; and 5) a low signal-to-noise ratio caused by a large culture volume hampers studies on biomarker kinetics. Compared with transwell cultures, the AM-OOC model uses a significantly fewer number of cells (2-fold lower than 24-well transwell culture), which is important because the cell source is quite limited from the human amnion membrane. Additionally, it allows for better interactions between cell layers while providing sensitive measurement capabilities of membrane permeability, biomolecule propagation (e.g., cytokines, growth factors, extracellular vesicles), and signaling pathways. Overcoming the limitations of conventional approaches, the developed AM-OOC allows for real-time in-depth imaging of cellular processes while controlling fluid and treatment flow in coculture chambers that are physically and fluidically isolated yet still allow cell-cell communication. These unique features of the developed AM-OOC allow analysis of complex interconnected biochemical and physiologic responses while maintaining cell viability.

The particular model presented herein is focused on visualizing cellular migration and transition, and, therefore, contains a few limitations for conducting other types of studies. In utero amnion membranes include AECs connected to an ECM containing AMCs by a 13-mm thick basement membrane. Although type IV collagen was included in between cell layers, the ECM fabric where AMCs are often located is not included in the model, and the influence of that component in migration and transition is still unclear. Thus, improvement to the device are envisioned to include: 1) shortening the microchannels to properly represent MFs; 2) adding dynamic medium flow to the AEC chamber to induce cellular shear stress normally impacted on AECs by amniotic fluid; and 3) fabrication of additional chambers to culture primary chorion trophoblast and decidual cells. Such improvements will result in recreating the full fetal membrane on OOC format.

The AM-OOC method developed herein overcomes several limitations of traditional 2D and 3D culture systems in investigating amnion membrane cellular and collagen characteristics and interactions. It is envisioned that future designs of this model will include the fetal membrane cells as well as a decidual layer to represent the full fetomaternal interface to study their functions during physiologic and pathologic pregnancies.

Additional Examples

The placenta and fetal membrane act as a protective barrier throughout pregnancy while maintaining communication and nutrient exchange between the baby and the mother. Disruption of this barrier leads to various pregnancy complications, including preterm birth, which can have lasting negative consequences on the health of the baby. Thus, understanding the role of the fetomaternal interface during pregnancy and parturition is useful in advancing basic and clinical research in the field of obstetrics.

However, human subject studies are difficult, and appropriate animal models are lacking. Non-human primate models that better mimic human pregnancy can be utilized, but is cost prohibitive in many cases. Due to these challenges, cell culture-based studies are most commonly utilized. However, the structure and functions of conventionally used 2D or 3D culture models are vastly different than those seen in vivo (in human), making it difficult to fully understand the various factors affecting pregnancy as well as pathways and mechanisms contributing to term and preterm births. This limitation also makes it difficult to develop new therapeutics, as suitable models are lacking.

OOC platforms can better recapitulate in vivo structure, functions, and responses of animal and human, and has already made significant contributions in research and development on various organ systems. Although many fields have seen the development and advancement of OOC platforms to model physiological and pathological states of their organ systems of interest, the area of obstetrics is only now applying this emerging technique to study pregnancy and preterm birth. The present disclosure demonstrates the development of feto-maternal interface OOC models (i.e., cervix-on-chip, placenta-on-chip, fetal membrane-on-chip) that mimics the three interfaces that are typically relevant to pregnancy, namely the cervix, placenta, and fetal membrane. These models can either be utilized individually or in combination to study different aspects of pregnancy. A common feature of the models described herein are that they are all based on multi-compartment coculture models interconnected with arrays of microfluidic channels that allow each cell types to be cultured within their compartments, yet allow interaction between the compartments biochemically as well as through cell migration. These OOC models better recapitulate both health and "disease state" of pregnancy and can be used broadly for basic science, translational, and clinical research, including, but not limited to, various drug screening for new therapeutic development as well as toxin screening, for example.

OOCs are beginning to become widely accepted as model systems that can better recapitulate human physiology, both in a healthy state as well as in a diseased state. These systems also allow easy experimental manipulation and analysis compared to conventional in vitro and in vivo model systems. These systems also have extremely broad applicability, from basic science to clinical research and drug development. Thus, these systems can be utilized by basic researchers, pharmaceutical companies, and regulatory agencies (e.g., the Food and Drug Administration and the Environmental Protection Agency). Due to these facts, in the past several years many companies focused on OOC development have been emerging, with major pharmaceutical companies, and some regulatory agencies, being their clients. However, no commercially available OOCs currently exist that mimic the feto-maternal interface, and also none related to pregnancy and preterm birth.

The OOC systems presented herein can be utilized as cornerstone platforms for the development of a range of OOCs mimicking physiological and pathological intrauterine tissue, which can be utilized to replace animal testing, accelerate understanding of feto-maternal communication, induction of preterm labor, drug or toxicant permeability at this vital interface, and development of new therapeutic strategies. These OOCs disclosed herein can be utilized individually or in an integrated multi-organ system form. These are: two-chamber amnion membrane OOC system, feto-maternal interface OOC system, placenta OOC system, cervix OOC system, and interconnected multi-organ OOC system.

Amnion Membrane OOC System: Two-Chamber Model

The AM-OOC system utilizes a planar parallel coculture OOC model design, having two circular culture chambers with interconnected microchannel array in between that functions as a controlled permeable barrier between the compartments. By culturing primary human AECs in the outer circular chamber and AMCs in the inner circular chamber, separated by type IV collagen-filled microchannels mimicking the basement membrane, the systems were able to recreate the amnion membrane on an OOC format. Here, primary AECs and AMCs obtained from the mid-zones of term not in labor fetal membranes were utilized. This model was successfully utilized to show the interactive and transitional properties of amnion cells (epithelial-to-mesenchymal transition and mesenchymal-to-epithelial transition) under normal and oxidative stress conditions, similar to how they behave and respond in utero. Specifically, when grown independently, AECs transitioned to AMCs and migrated, while AMCs migrated without transition. OS caused AECs' transition but prevented migration, whereas AMCs' migration was unhindered. Coculture of cells facilitated transition, migration, and eventual integration in the contiguous population. OS cotreatment in both chambers facilitated AECs' transition, prevented migration, and increased inflammation, a process that was prevented by NAC. In conclusion, the AM-OOC recapitulated cellular mechanisms observed in utero and enabled experimental manipulation of cells to determine their roles during pregnancy and parturition. Results and designs are shown in FIGS. 7A-7C and FIG. 8.

Figure 8:
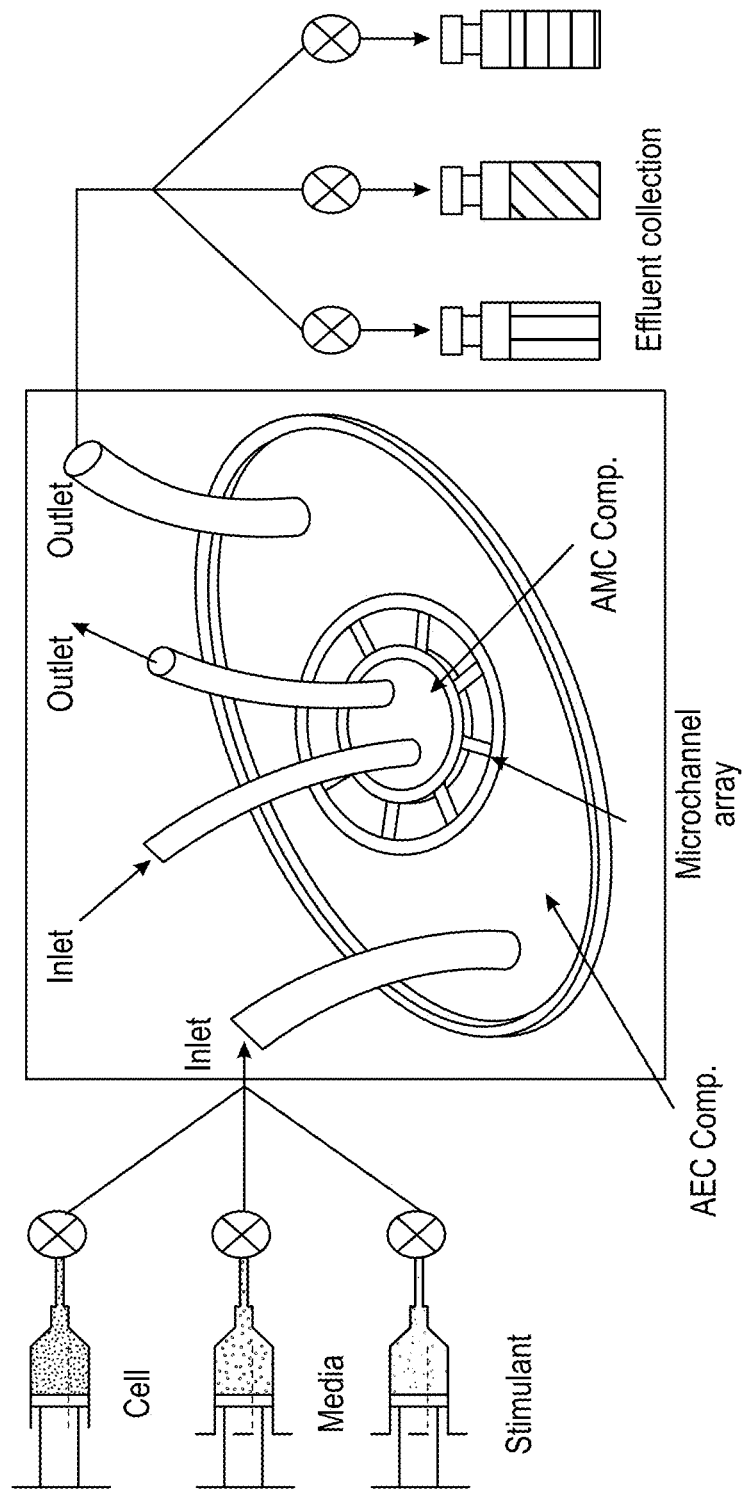
FIG. 8 illustrates a dynamic fetal membrane organ-on-chip (OOC) device, showing a center AMC compartment connected to the outer AEC compartment through arrays of microfluidic channels that work as a diffusion barrier. Inlets for each compartment are connected through multiple syringes to deliver cells, culture media, and stimulants (shown only for AEC). The outlets are connected to one or more effluent collection tubes (shown only for AEC). All microfluidic operations are controlled through computer-controlled microvalves and syringes.

A variation in the operation of the two-chamber device is shown in FIG. 8. Here, instead of loading media and collecting them through a pipette, as was done in the case of FIG. 7, syringe pumps providing media to the culture compartments through tubing connections are shown. At the outlet of the tubing are effluent collection chambers so that used culture media can be analyzed.

Figure 9:
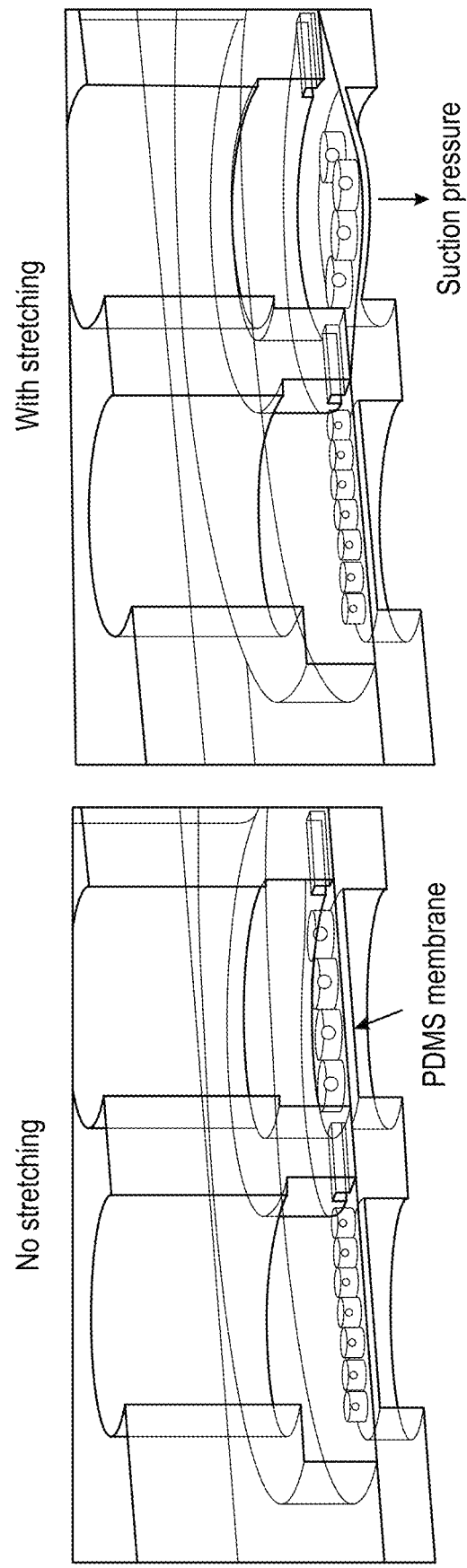
FIG. 9 illustrates a two-chamber device where cells are cultured on a flexible membrane underneath where pneumatically controllable microchannels are placed. Applying negative pressure through this channel will deflect the membrane downwards, applying stretching motion to the cells cultured on the membrane.

A variation of this device is one that can apply stretching to cells during culture. FIG. 9 shows a design that allows application of a stretching motion to the cells being cultured (only two chambers shown for illustration purposes). Here, a thin PDMS membrane (20-50 μm) can replace the solid PDMS substrate on which cells are cultured, and a pneumatically actuated microchannel will be placed underneath. Applying suction pressure through this pneumatic actuation channel to the PDMS membrane will result in the membrane being deflected downward, which will result in applying the stretching motion to the cells being cultured on these membranes. This motion is similar to the stretching motion that a fetal membrane experiences throughout pregnancy. Three independent pneumatic actuation channels can be utilized under each of the three culture chambers to allow independent control of the three culture chambers, if desired. The PDMS membrane will be fabricated by spin-coating liquid-state PDMS on a substrate, which will then be placed on top of the pneumatic actuation channel.

Feto-Maternal Interface OOC System: Four-Chamber Model

Figure 10:
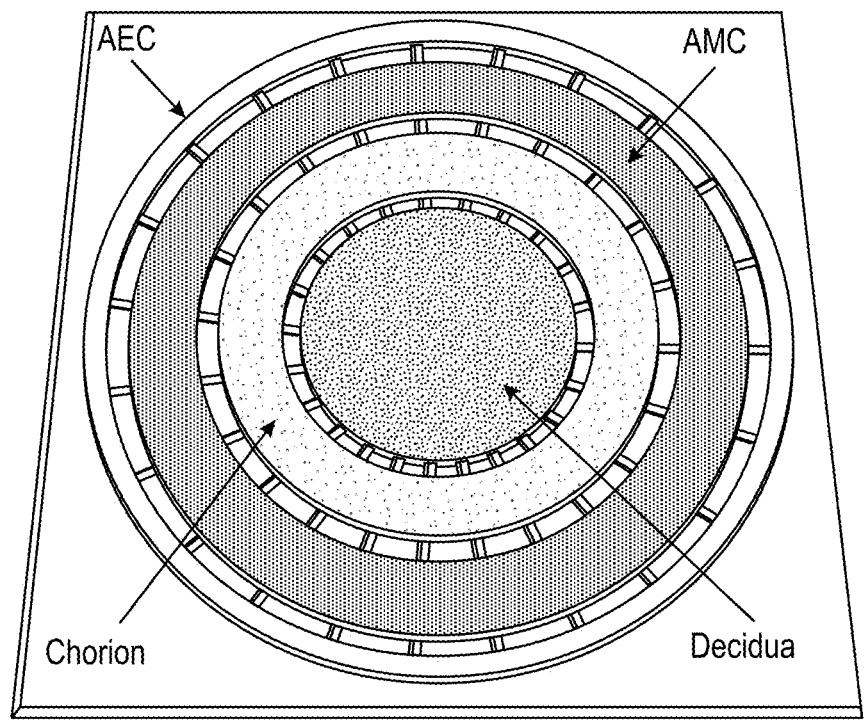
FIG. 10 illustrates a four-chamber fetal membrane-decidua interface model (FMI-OOC) device, showing four circular co-culture compartments interconnected through arrays of microfluidic channels.
Figure 11:
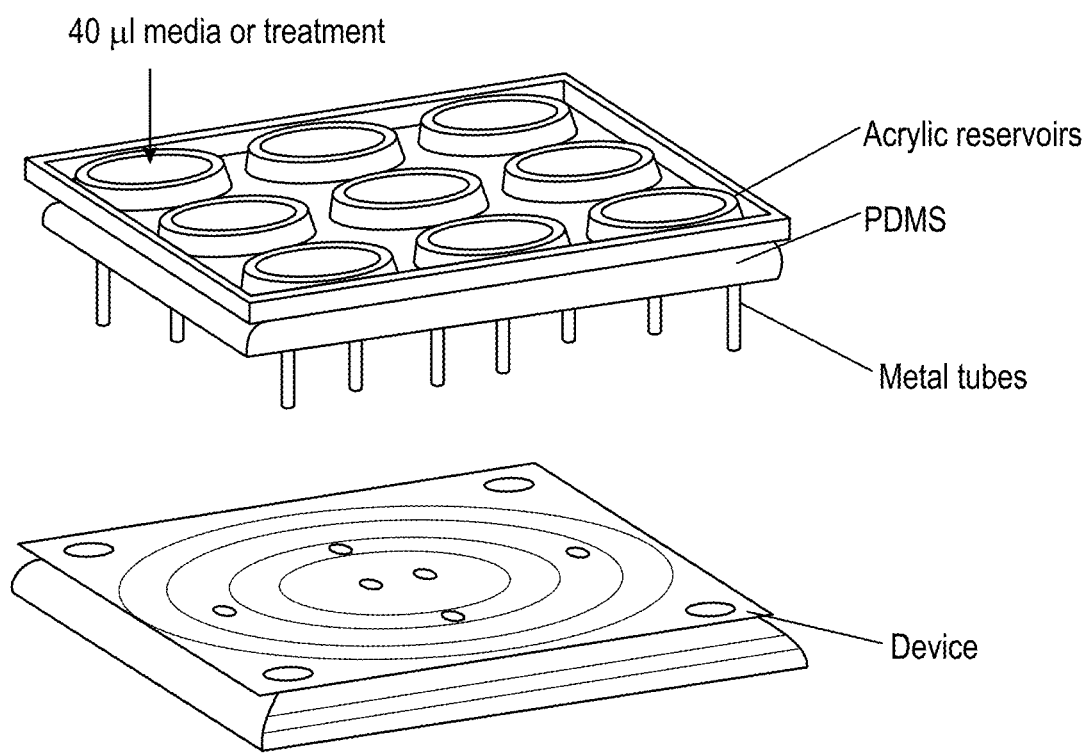
FIG. 11 illustrates an on-chip reservoir array block integrated with the OOC device.
Figure 12A:
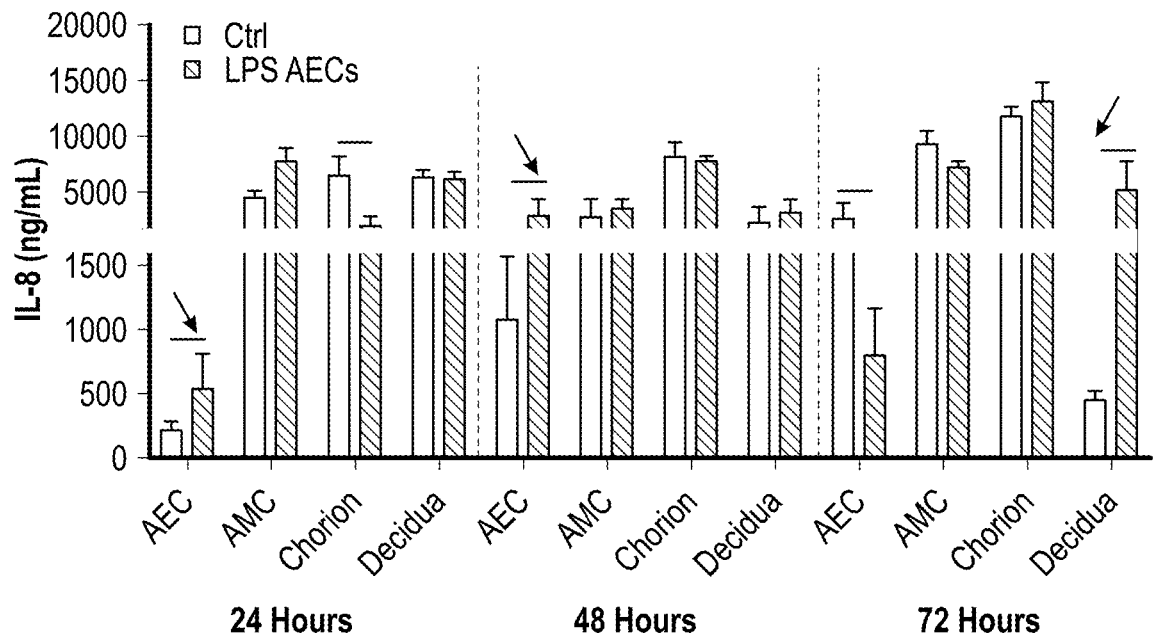
FIG. 12A illustrates after lipopolysaccharide (LPS) treatment in the AEC chamber for 24, 48, or 72 hours, cell supernatants were collected from each cell chamber within the FMI-OOC to document LPS induced inflammation propagation. LPS induced an increase in AEC IL-8 production at 24 and 48 hours, which reached the maternal decidua chamber by 72 hours, causing an increase in IL-8. Documenting LPS induced fetal inflammation can reach the maternal compartment in 72 hours within an FMI-OOC device.
Figure 12B:
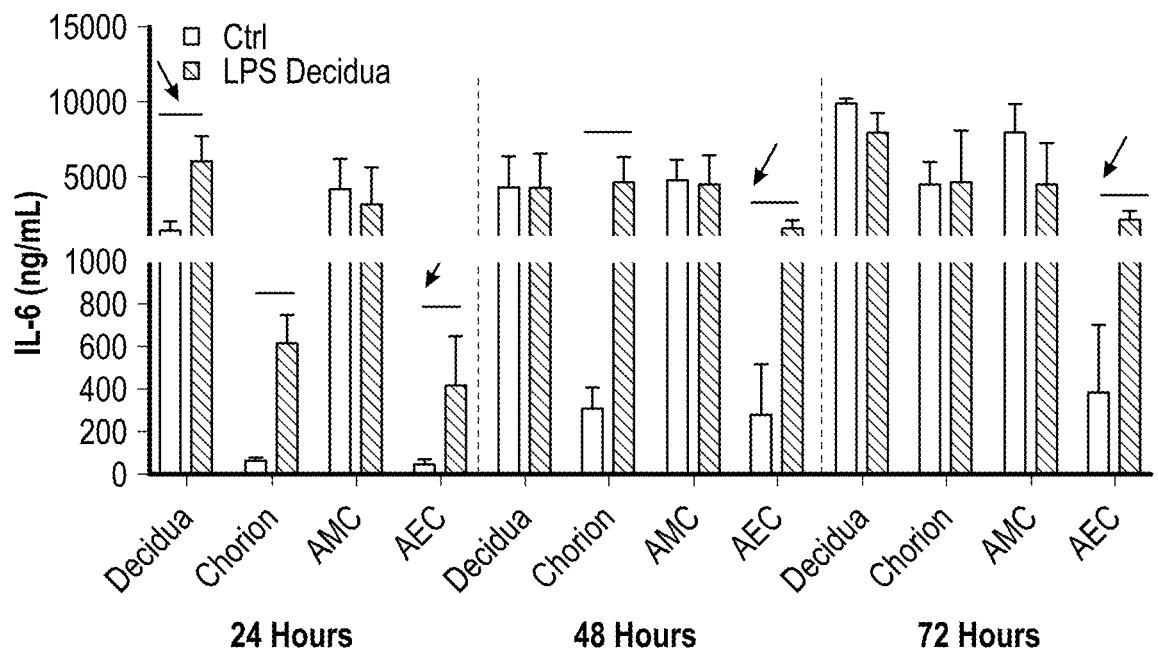
FIG. 12B illustrates after LPS treatment in the maternal decidua (DECI) chamber for 24, 48, or 72 hours, cell supernatants were collected from each cell chamber within the FMI-OOC to document LPS induced inflammation propagation. LPS induced an increase in DECI IL-6 production at 24, which reached the fetal AEC chamber by 24 hours, causing a rise in IL-8 that increased over 72 hours. Documenting LPS induced maternal inflammation can reach the fetal compartment in 72 hours within an FMI-OOC device.

The AM-OOC model does not contain maternal components. The device described here expands the previously described two-chamber coculture model into a four-chamber coculture model to include both fetal and maternal cell components. The fetal membrane-decidua interface model (FMI-OOC) composed of four coculture compartments interconnected through arrays of microfluidic channels (FIG. 10 and FIG. 11). Here, three cell types from the fetal side (AEC, AMC, chorion mesenchymal cells (CMC)/chorion trophoblast (CT)) and one from the maternal side (decidua cells) were used, establishing the first OOC model that contains both fetal and maternal cells. Cell loading concentration into each chamber mimicked those of in utero cell ratios of the fetal membrane tissue. The microfluidic channel array prevents cells from flowing into the neighboring compartments during initial cell loading, allow localized drug treatment of each cell layer, and allow taking supernatant from each layer independently for local biochemical analysis. At the same time, these channels allow biochemicals to diffuse between the layers, and also permit cell migration and transition. Taken together, this structure is similar to having distinct cell layers, as seen in the membrane-decidua F-M interface. Data using this model over a 5-7 days culture period was able to demonstrate the ability to create F-M uterine infections and the model's capability in measuring the extent of inflammation at each layer when infection or OS occurs at either the fetal or maternal side (FIGS. 12A-12B). This shows that an infection-induced pathological state of F-M was successfully established in the OOC model.

A variation of this F-M interface model is to create an array of rectangular chambers that are used for high throughput screening instead of using concentric-shaped culture chambers. The fundamental design remains the same, where culture chambers are connected through arrays of microfluidic channels.

Placenta-Decidua Interface-OOC (Pi-OOC) Model: Four-Chamber Model

Figure 13A:
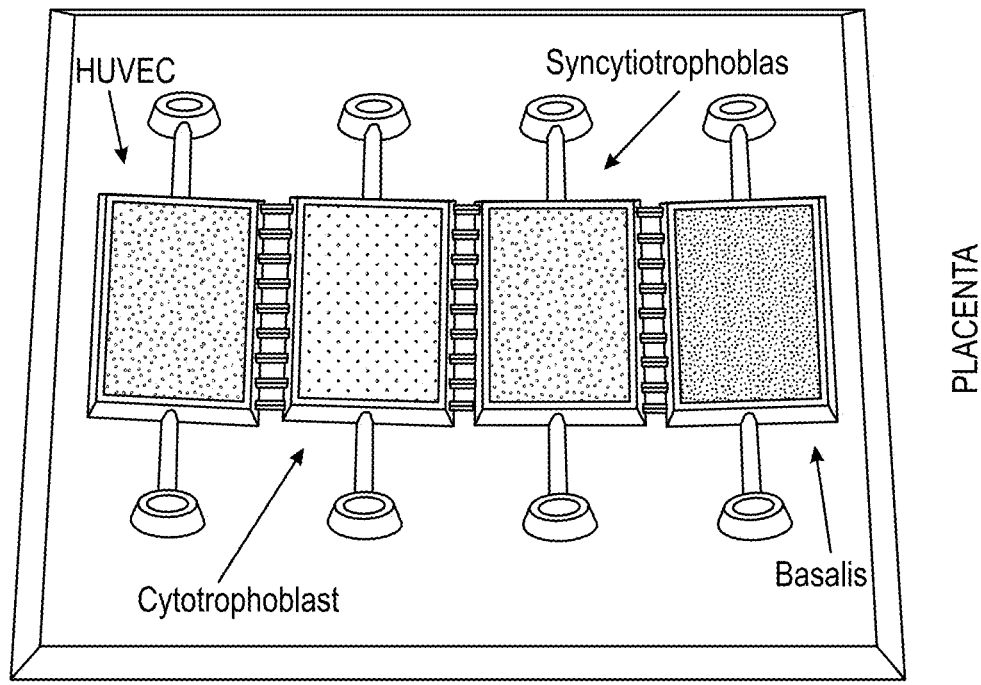
FIG. 13A illustrates a four-compartment placenta-decidua interface-OOC (PI-OOC).
Figure 13B:
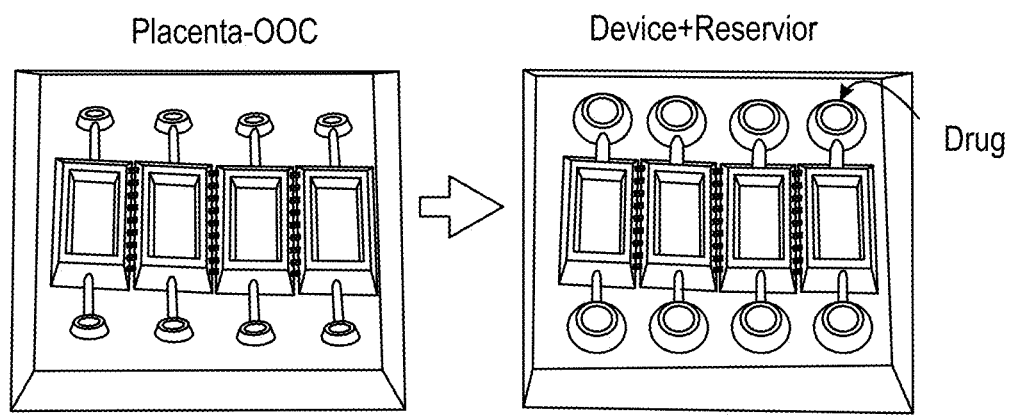
FIG. 13B illustrates after cell loading, a reservoir layer will be bonded on top of the device and then reservoirs filled with culture media or drug so that the device can operate for up to 24 hours without adding new culture media.
Figure 14A:
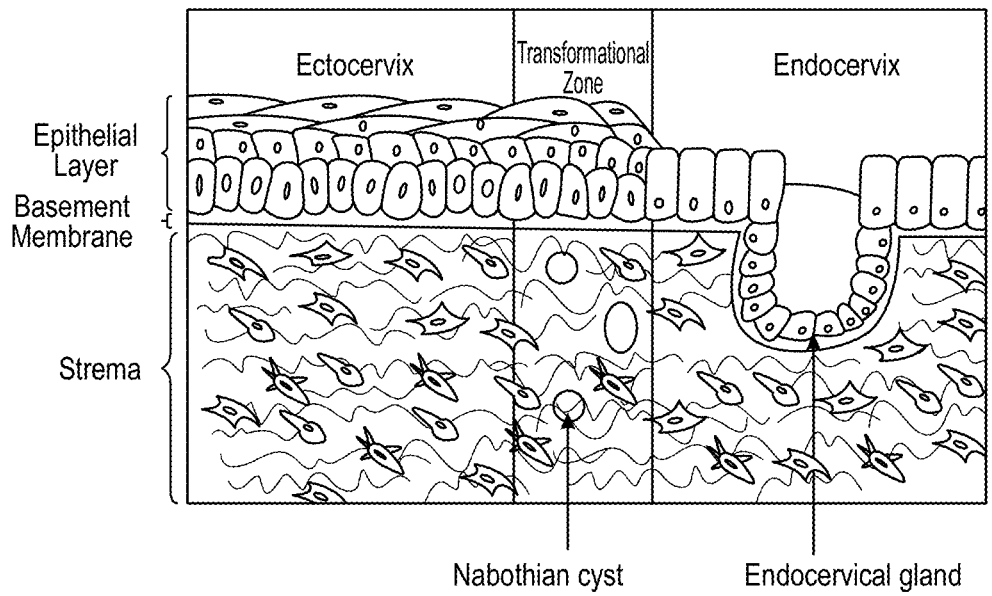
FIGS. 14A-14D illustrate a cervix on a chip model using a microchannel array-based co-culture model.
Figure 14B:
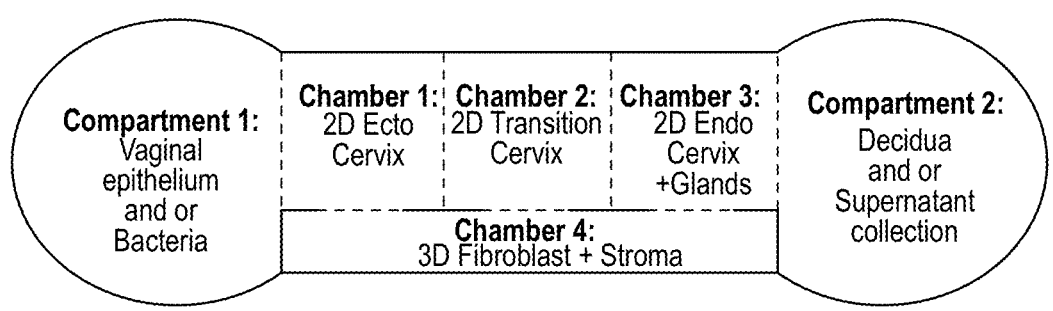
Figure 14C:
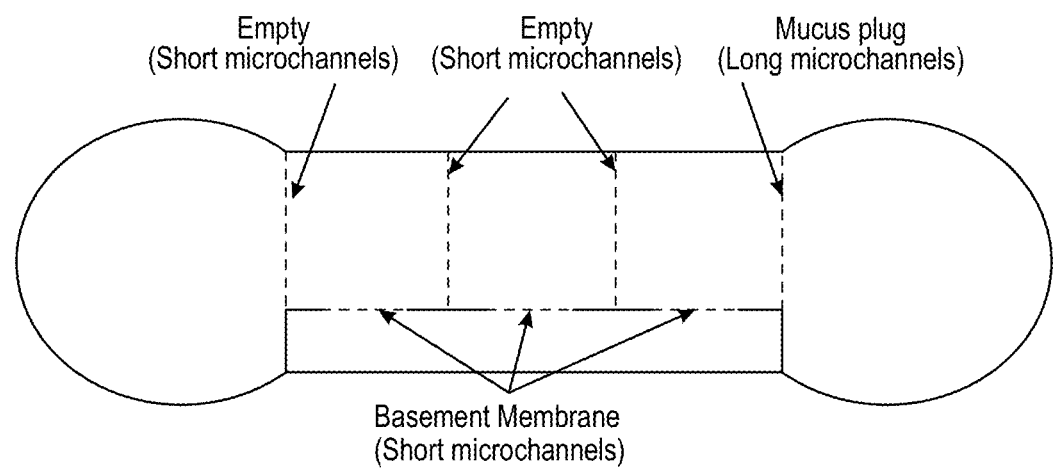
Figure 14D:
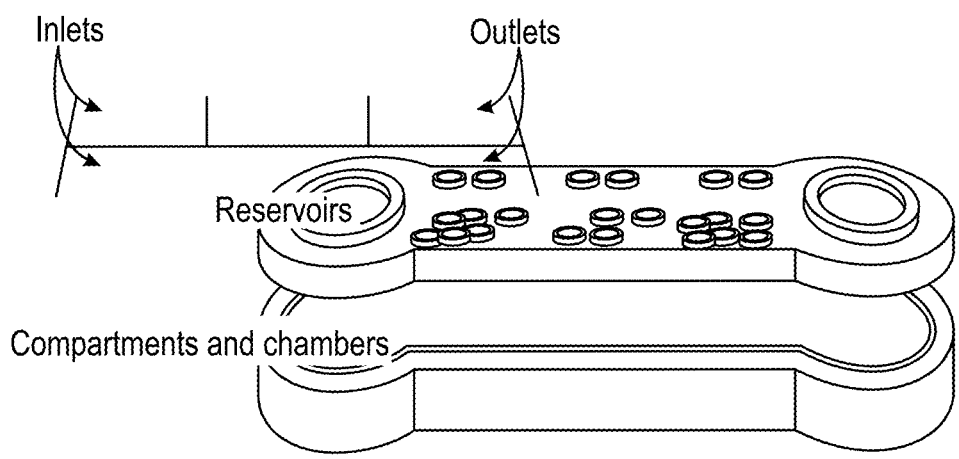

FIGS. 13A-13B show a four-compartment placenta Interface-OOC (Pi-OOC) model design, composed of four rectangular culture compartments interconnected through arrays of microfluidic channels. These chambers represent the maternal decidua basalis→placental syncytiotrophoblast-→cytotrophoblast, and human umbilical vessel endothelial cell (HUVECs) layers. The layout and dimensions of the four compartments are designed to create a uniform layout for cell culture, and to fit within a well of a 6-well culture plate. A variation of this embodiment is where different cells are cultured, for example AECs, AMCs, chorion, and decidua cells. The chamber design is not limited to four culture chambers. Rather, it can be combinations of any number of cell culture chambers and microchannels. For example, a two-chamber co-culture model that uses chorion cells in one chamber and Decidua cells in another chamber is an example. In another example, a three-chamber co-culture model is used, composed of syncytio-trophoblast cell culture chamber, a cytotrophoblast cell culture chamber, and a HUVEC cell culture chamber. In yet another example, a five-chamber co-culture model is used, composed of a decidua cell culture chamber, a decidua-syncytio-trophoblast co-culture chamber, a syncytiotrophoblast cell culture chamber, a cytotrophoblast cell culture chamber, a fibroblast cell culture chamber, and a HUVEC cell culture chamber. The culture conditions of these models, for example culture media or gas concentration (carbon dioxide, oxygen) can also be varied depending on the application need, such as for example studying a specific gestational timepoint where the needed gas condition differs. Here, the array of 24 microfluidic channels (5 μm height, 30 μm width, and 600 μm length) function similar to the ones in previous OOC models, allowing localized cell loading and culture as well as localized biochemical analysis, while still allowing cell migration and biochemical diffusion between compartments. Entactin-collagen IV-laminin (E-C-L, Millipore) solution are diluted in a sterile serum-free medium for each cell line up to a final concentration of 10 μg/mL. Both sides of the membrane are be coated with E-C-L solution, prior to use. Cell loading concentration into each chamber mimic those of in utero cell ratios of the placenta and umbilical cord. HUVEC and trophoblasts represent endothelium and epithelium of the interface, and trophoblast will provide barrier functions. This setup is similar to having distinct cell layers with semipermeable cell barriers, as seen in the human placenta and some advanced OOC models. As an alternative to the microchannel array that is placed on the bottom of the device, arrays of microchannels can be positioned in the middle of the culture chamber diving barrier, where such chamber barrier can have angles different from 90°. Such sloped microchannel structure can be printed using a sub-micrometer-resolution 3D printer (Nanoscribe Photonics GT2).

Each rectangular culture compartment will have inlet/outlets to load cells, apply culture media and stimulants, take out effluent for biochemical assays, and to conduct end-point immune-fluorescent staining of the cells in the chip. To simplify device operation without the need for tubing or syringe pumps, a media/effluent reservoir array block can be placed on top of the main Pi-OOC so that all operations can be conducted utilizing pipetting-based cell/reagent handling. This mode of pumpless operation is what allows 30-60 devices to be tested in parallel in one experimental run due to its simplicity in operation, something that is not possible when devices must operate with complex tubing connections and syringe pumps. For the OOCs, type IV collagen matrigel are loaded into the microchannels. Cells are then be loaded into each compartment. Next, the culture media reservoir block is placed on top of the OOC device and bonded together (after plasma treatment of the reservoir layer to enhance bonding). The media height differences and microfluidic channel dimensions/numbers are adjusted to control the diffusion time between the compartments as desired.

A variation of the above embodiment is where multiple models are interconnected through parallel channels, so that multiple independent and/or semi-independent experiments can be conducted in parallel.

Cervix on a Chip Model: Four-Chamber Model

In another variation of the co-culture model, a cervix on a chip OOC model was designed. Intrauterine infection and/or inflammation account for almost 40% of preterm births. Ascending vaginal infection is hypothesized to be the most common pathway of intrauterine infection. This model accommodates cells and tissues that may mimic the physiologic conditions as well as ascending vaginal-cervical infection and thus bridge the gap between animal models and human-based clinical trials. FIGS. 14A-14D illustrate such a model.

Integrated Organ-Chip Models

Figure 15A:
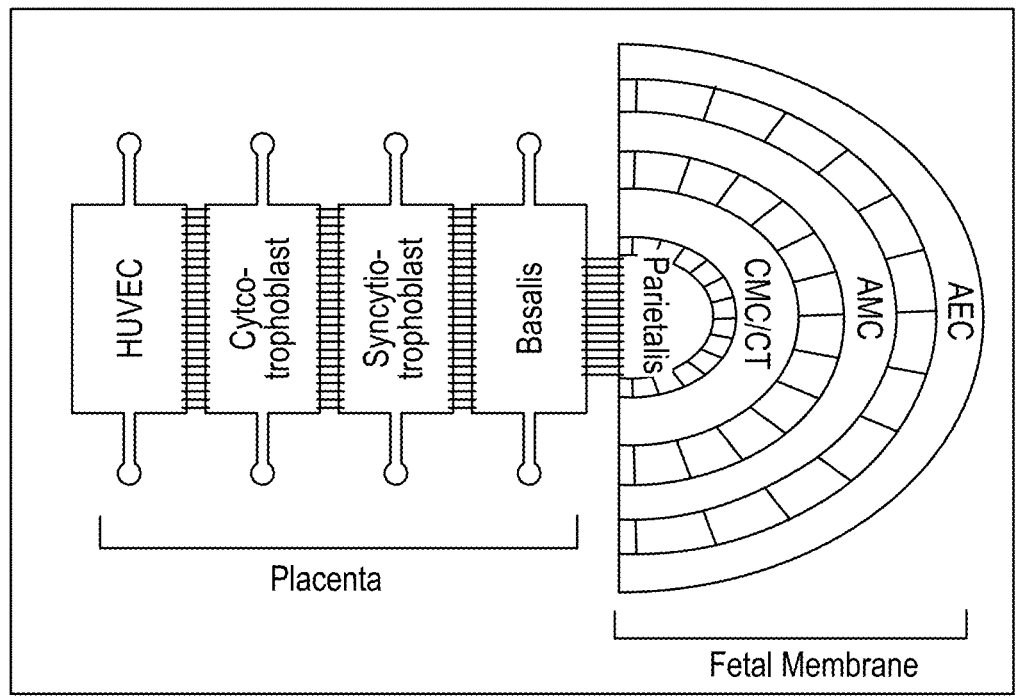
FIGS. 15A-15B illustrate integrated multi-organ feto-maternal interface organ-on-chip schematics.
Figure 15B:
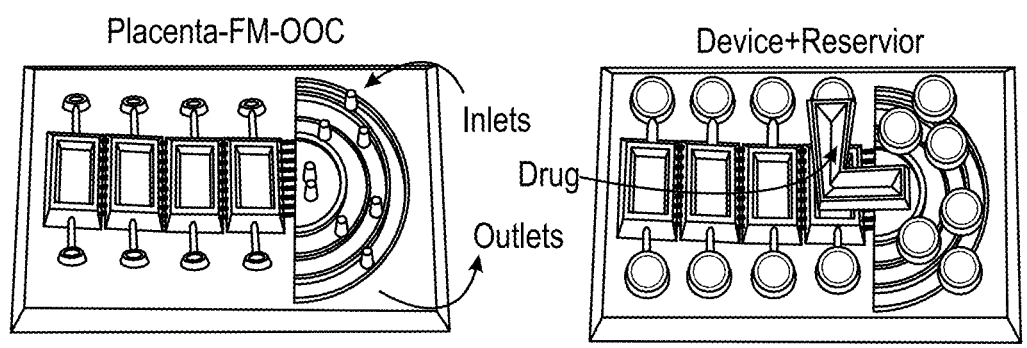
Figure 16:
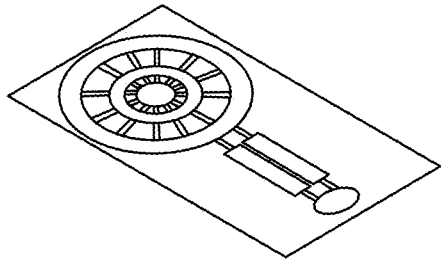
FIG. 16 illustrates an integrated OOC model that shows fetal membrane+cervix on a chip, and palcenta+fetal membrane+cervix on a chip.
Figure 16:
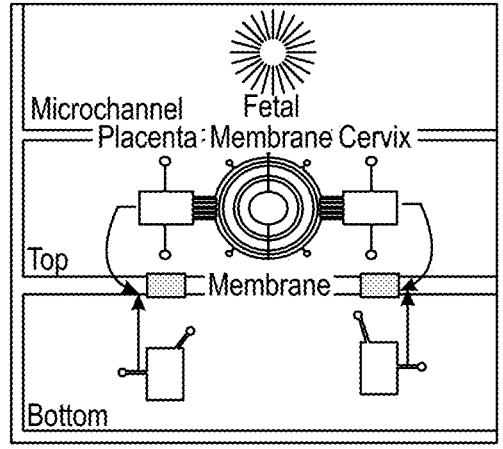
Figure 16:
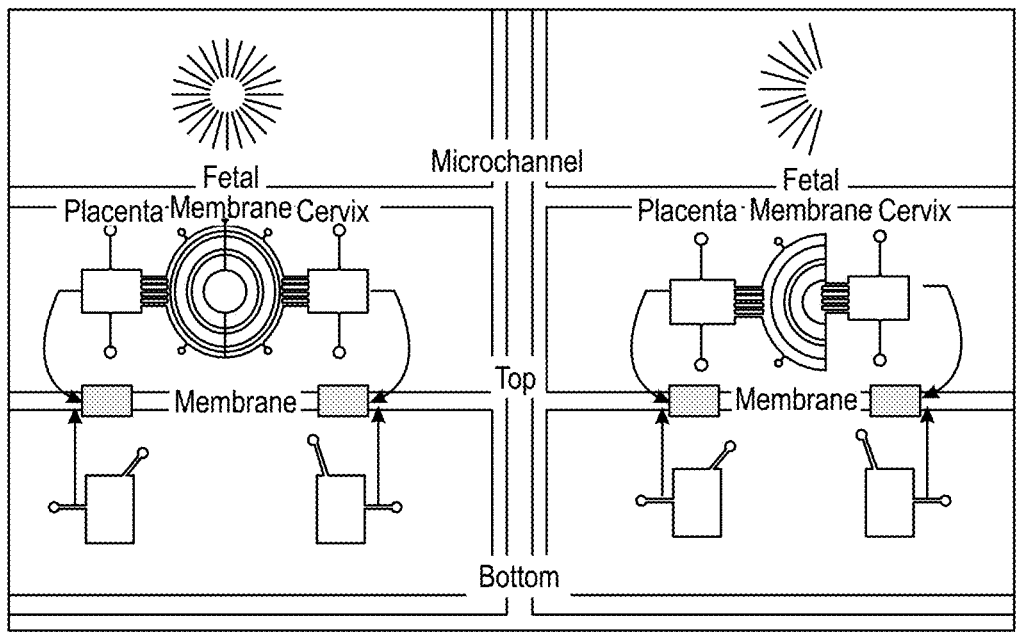
Figure 16:
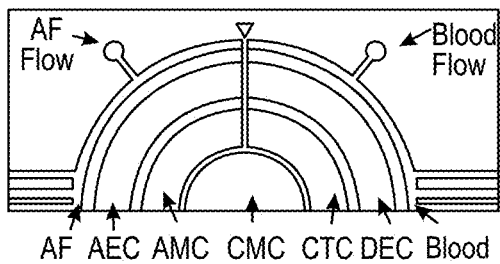
Figure 16:
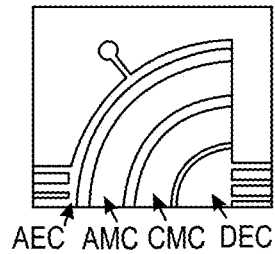

The OOC models described herein can be integrated in various combinations to mimic the organ system as a whole. For example, to study both the placenta and fetal membranes separately as well as together due to their proximity in utero, and to also gain an understanding of the F-M interface crosstalk during statin treatment. FIGS. 15A-15B show an eight-compartment multi-organ feto-maternal interface OOC (PI-FMI-OOC) design, composed of four rectangle cell culture chambers for placental cells and four elliptical cell culture chambers for fetal membrane-derived cells, all interconnected through arrays of microfluidic channels. Here, the array has 24 microfluidic channels, each having a dimension of about 30 μm width, 5 μm height, and 600 μm length. This integrated OOC model can contain physiologically relevant cell layers as identified in two individual F-M interface models. The placenta and fetal membranes care connected through distinct decidua layers, the basalis and parietalis, mimicking the vascular junction in utero that delivers drug and other nutrients to both F-M interfaces. A media/effluent reservoir array block is placed on top of the device to facilitate drug treatment, effluent collection, and cell collection at different time points. A different combination for an integrated OOC model is shown in FIG. 16. Other variations of the organ-chip model disclosed here can be interconnected in different combinations.

Disease State Organ-Chip Models

For each of the OOC model described in detail above, both healthy states and diseased states can be created. To create a diseased state, for example, that of infection, molecules such as cigarette smoke extract that can cause oxidative stress or LPS that mimics bacterial infection, can be applied to any of the cellular layer. This will create a disease state of the OOC models, functioning as a model of preterm birth.

In view of the aforementioned, in an embodiment, the present disclosure pertains to an organ-chip model of amnion membrane. In some embodiments, the organ-chip model includes two cell culture chambers connected through arrays of microfluidic channels. In some embodiments, the cell culture chambers are circular or curved in nature to minimize dead volume and allow efficient and uniform cell loading. In some embodiments, the cell culture chambers are rectangular in nature. In some embodiments, the arrays of microfluidic channels are sufficiently shallow to prevent cells from moving from one compartment to another compartment during the initial cell loading process. In some embodiments, the arrays of microfluidic channels are sufficiently large enough to allow biochemicals to diffuse through the two cell culture chambers. In some embodiments, the arrays of microfluidic channels are sufficiently large enough to allow cells to migrate from one compartment to another compartment. In some embodiments, the number and dimension of the arrays of microfluidic channels are adjusted to control the diffusion time between the two cell culture chambers. In some embodiments, the microfluidic channels are filled with various extracellular matrixes. In some embodiments, cell culture media is perfused through a syringe pump connected to a compartment and effluent is collected from another compartment. In some embodiments, effluent can be collected at different time point to allow biochemical analysis of a supernatant.

In some embodiments, cell culture media and collection reservoirs are utilized such that passive diffusion can provide the cell culture media to cells. In some embodiments, the cell culture chambers can be filled to different height to allow control over diffusion. In some embodiments, at least one media reservoir can be periodically filled with at least one of new culture media and other biochemicals. In some embodiments, the other biochemicals can include, without limitation, drugs, harmful substances, and combinations thereof. In some embodiments, effluent can be collected at different time points. In some embodiments, the organ-chip model further includes an additional layer having culture media reservoirs integrated on top of the organ-chip model, and inlet and outlets are aligned together. In some embodiments, fluorescent tagging of cells being grown in the organ-chip model is conducted to visualize cells migrating between culture compartments. In some embodiments, immunostaining of cells within the organ-chip model can be conducted by loading various biochemicals needed for immunostaining of the cells through inlets or a media reservoir. In some embodiments, a first cell culture chamber is loaded with amnion epithelial cells (AECs) and a second cell culture chamber is loaded with amnion mesenchymal cells (AMCs), In another embodiment, the present disclosure pertains to an organ-chip model of the feto-maternal interface (fetal membrane-decidua parietalis). In some embodiments, the organ-chip model includes four or more cell culture chambers connected through arrays of microfluidic channels. In some embodiments, the four or more cell culture chambers are circular or curved in nature to minimize dead volume and also allow efficient and uniform cell loading. In some embodiments, the four or more cell culture chambers are rectangular in nature. In some embodiments, the four or more cell culture chambers are ring shaped allowing each of the four or more cell culture chambers to be placed within a ring of another of the four or more cell culture chambers. In some embodiments, the arrays of microfluidic channels are sufficiently shallow to prevent cells from moving from one compartment to another compartment during initial cell loading process. In some embodiments, the arrays of microfluidic channels are sufficiently large enough to allow biochemicals to diffuse through between two compartments or allow cells to migrate from one compartment to another compartment. In some embodiments, a number and dimension of the arrays of microfluidic channels can be adjusted to control diffusion time between compartments. In some embodiments, the microfluidic channels may be filled with various extracellular matrixes.

In some embodiments, cell culture media is perfused through a syringe pump connected to at least one compartment, and effluent is collected from another compartment. In some embodiments, the effluent can be collected at different time point to allow biochemical analysis of supernatant. In some embodiments, cell culture media and collection reservoirs are placed on top of inlets and outlets of at least one of the cell culture chambers such that passive diffusion is utilized to provide the cell culture media to cells. In some embodiments, at least one of the cell culture chambers is operable to be filled to different heights to allow control over diffusion. In some embodiments, a media reservoir can be periodically filled with new culture media or other biochemicals. In some embodiments, the other biochemicals can include, without limitation, drugs, harmful substances, and combinations thereof. In some embodiments, effluent can be collected from reservoirs at different time points. In some embodiments, immunostaining of cells within the organ-chip model is conducted by loading biochemicals needed for immunostaining cells through inlets or a media reservoir. In some embodiments, each cell culture compartment can be filled with cells from a fetal side and from a maternal side. In some embodiments, the cells can include, without limitation, amnion epithelial cells (AEC), amnion mesenchymal cells (AMC), chorion mesenchymal cells (CMC)/chorion trophoblast (CT), decidua parietalis cells, and combinations thereof.

In a further embodiment, the present disclosure pertains to an organ-chip model of a feto-maternal interface (placenta-decidua interface). In some embodiments, the organ-chip model includes four or more cell culture chambers connected through arrays of microfluidic channels. In some embodiments, the four or more cell culture chambers are circular or curved in nature to minimize dead volume and allow for efficient and uniform cell loading. In some embodiments, the four or more cell culture chambers are rectangular in nature. In some embodiments, the four or more cell culture chambers are ring shaped allowing each cell culture chamber of the four or more cell culture chambers to be placed within another cell culture chamber of the four or more cell culture chambers. In some embodiments, the arrays of microfluidic channels are sufficiently shallow to prevent cells from moving from one compartment to another compartment during initial cell loading process. In some embodiments, the arrays of microfluidic channels are sufficiently large enough to allow biochemicals to diffuse through between two compartments or allow cells to migrate from one compartment to another compartment. In some embodiments, a number and dimension of the arrays of microfluidic channels can be adjusted to control diffusion time between compartments. In some embodiments, the arrays of microfluidic channels are filled with various extracellular matrixes.

In some embodiments, cell culture media is perfused through a syringe pump connected to one compartment and effluent is collected from another compartment. In some embodiments, effluent can be collected at different time points to allow biochemical analysis of supernatant. In some embodiments, cell culture media and collection reservoirs are placed on top of inlets and outlets of cell culture chambers such that passive diffusion is utilized to provide the cell culture media to cells. In some embodiments, at least one of the four or more cell culture chambers are adapted to be filled to different heights to allow control over diffusion. In some embodiments, a media reservoir is periodically filled with new culture media or other biochemicals. In some embodiments, the other biochemical can include, without limitation, drugs, harmful substances, and combinations thereof. In some embodiments, effluent is collected from reservoirs at different time points. In some embodiments, immunostaining of cells within the organ-chip model is conducted by loading various biochemicals needed for immunostaining of the cells through inlets or a media reservoir. In some embodiments, each cell culture chamber of the four or more cell culture chambers is filled with cells that can include, without limitation, maternal decidua basalis, placental syncytiotrophoblast, cytotrophoblast, human umbilical vessel endothelial cell (HUVECs), and combinations thereof. In some embodiments, the organ-chip model includes two or more cell culture chambers connected through arrays of microfluidic channels. In some embodiments, the organ-chip model includes six or more cell culture chambers connected through the arrays of microfluidic channels. In some embodiments, the two or more cell culture chambers are circular or curved in nature to minimize dead volume and for allow efficient and uniform cell loading. In some embodiments, the two or more cell culture chambers are rectangular in nature.

In some embodiments, the cell culture chambers are arranged in any arrangements that best mimic the cervix structure and functions. In some embodiments, the arrays of microfluidic channels is sufficiently shallow to prevent cells from moving from one compartment to another compartment during initial cell loading. In some embodiments, the arrays of microfluidic channels is sufficiently large enough to allow biochemicals to diffuse through between the two or more cell culture chambers or allow cells to migrate from one compartment to another compartment. In some embodiments, a number and dimension of the arrays of microfluidic channels can be adjusted to control diffusion time between compartments. In some embodiments, the arrays of microfluidic channels are filled with an extracellular matrix. In some embodiments, cell culture media is perfused through a syringe pump connected to one compartment and effluent is collected from another compartment. In some embodiments, effluent is collected at different time points to allow biochemical analysis of supernatant. In some embodiments, cell culture media and collection reservoirs are placed on top of inlets and outlets of the two or more cell culture chambers such that passive diffusion is utilized to provide the cell culture media to cells. In some embodiments, cell culture media reservoirs are filled to different heights to allow for control over diffusion. In some embodiments, a media reservoir is periodically filled with new culture media or other biochemicals. In some embodiments, the other biochemicals can include, without limitation, drugs, harmful substances, and combinations thereof.

In some embodiments, effluent is collected from reservoirs at different time points. In some embodiments, immunostaining of cells within the organ-chip model can be conducted by loading various biochemicals needed for immunostaining of the cells through inlets or a media reservoir. In some embodiments, each cell culture chamber of the two or more cell culture chambers are filled with cells representing at least one of vaginal epithelium, cervix, endo-cervix, transitional-cervix, ecto-cervix, fibroblast, stroma, decidua, and combinations thereof. In some embodiments, a vaginal epithelium side of the two or more cell culture chambers is loaded with bacterial cells that represent at least one of a vaginal microbiome and invading bacterial pathogens. In some embodiments, the interconnected organ-chip model including a combination of one or more of the organ-chips models connected through arrays of microfluidic channels. In some embodiments, the arrays of microfluidic channels interconnect between culture compartments in the organ-chip models.

In some embodiments, the organ-chip models of the present disclosure can further include a bottom substrate. In some embodiments, the bottom substrate is a flexible membrane to allow for application of a stretching motion to cells during culture. In some embodiments, pneumatically actuated microchannels are placed below the flexible membrane and applying pneumatic pressure enables stretching of the flexible membranes. In some embodiments, one or more independently controlled microchannels allow for application of a stretching motion to only a desired cell culture compartment. In some embodiments, the organ-chip models of the present disclosure a diseased state is induced to create a disease stated organ-chip model. In some embodiments, application of biochemicals or toxins mimic bacterial infection or oxidative stress. In some embodiments, the biochemicals or toxins can include, without limitation, lipopolysaccharide (LPS), cigarette smoke extract (CSE), compounds that mimic oxidative stress, compounds that mimic sterile infection conditions, and combinations thereof.

In an additional embodiment, the present disclosure pertains to an organ-chip model including a plurality of cell culture chambers connected through a plurality of microfluidic channels. In some embodiments, each cell culture chamber of the plurality of cell culture chambers include an inlet and an outlet. In some embodiments, the inlet is configured to receive at least one of a cell, cell media, or a cell stimulant. In some embodiments, at least one outlet is configured to collect effluent. In some embodiments, each of the culture chambers has a shape that can include, without limitation, circular, oval, rectangular, ring-shaped, curve-shaped, and combinations thereof. In some embodiments, at least one microfluidic channel of the plurality of microfluidic channels is filled with extracellular matrixes. In some embodiments, at least one microfluidic channel of the plurality of microfluidic channels is in fluid communication with at least one cell culture chambers of the plurality of cell culture chambers. In some embodiments, the organ-chip model further includes a bottom substrate. In some embodiments, the bottom substrate is a flexible membrane to allow for application of a stretching motion to cells during culture.

Although various embodiments of the present disclosure have been illustrated in the accompanying Drawings and described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially", "approximately", "generally", and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a", "an", and other singular terms are intended to include the plural forms thereof unless specifically excluded.

What is claimed is:

1. An organ-chip model of human pregnancy and parturition comprising:
   a plurality of cell culture chambers connected through arrays of microfluidic channels that connect adjacent cell culture chambers and permit the passage of cells between the cell culture chambers;
   wherein each cell culture chamber of the plurality of cell culture chambers comprises an inlet and an outlet;
   wherein the inlet is configured to receive at least one of a cell, cell media, or a cell stimulant; and
   wherein at least one outlet is configured to collect effluent;
   wherein the organ-chip model is selected from the group consisting of an organ-chip model of amnion membrane, an organ-chip model of a feto-maternal interface (fetal membrane-decidua parietalis), an organ-chip model of a feto-maternal interface (placenta-decidua interface), an organ-chip model of a cervix, and combinations thereof;
   a bottom substrate, wherein the bottom substrate is a flexible membrane to allow for application of a stretching motion to cells during culture; and
   pneumatically actuated microchannels located below the flexible membrane.

2. The organ-chip model of claim 1, wherein the organ-chip model comprises an interconnected organ-chip model; wherein the interconnected organ-chip model comprises a combination of one or more organ-chip models connected through a plurality of microfluidic channels; and wherein the plurality of microfluidic channels interconnect between cell culture chambers in the one or more organ-chip models.

3. The organ-chip model of claim 1, wherein each cell culture chamber of the plurality of cell culture chambers has a shape selected from the group consisting of a circular shape, an oval shape, a rectangular shape, a ring-shape, a curve shape, and combinations thereof.

4. The organ-chip model of claim 1, wherein at least one microfluidic channel of the arrays of microfluidic channels is in fluid communication with at least one cell culture chamber of the plurality of cell culture chambers.

5. The organ-chip model of claim 1, wherein each microfluidic channel of the arrays of microfluidic channels are sized to control movement, wherein the movement is at least one of preventing movement from one cell culture chamber to another cell culture chamber during an initial cell loading process, allowing biochemicals to diffuse through at least one cell culture chamber of the plurality of cell culture chambers, or allowing cells to migrate from one cell culture chamber to another cell culture chamber.

6. The organ-chip model of claim 1, wherein each microfluidic channel of the arrays of microfluidic channels is sized to control cell movement, wherein the movement of cells can be controlled by the number, size, and shape of the microchannels.

7. The organ-chip model of claim 1, wherein the microfluidic channel is located in the middle of a barrier that separates a cell culture chamber from another, and wherein the barrier is vertical or has slopes having an angle of less than 90°.

8. The organ-chip model of claim 1, wherein number and dimension of the arrays of microfluidic channels are adjusted to control diffusion time between the plurality of cell culture chambers.

9. The organ-chip model of claim 1, wherein the at least one of a cell, cell media, or a cell stimulant is perfused through a syringe pump connected to an inlet of one cell culture chamber and the effluent is collected from an outlet of another cell culture chamber.

10. The organ-chip model of claim 1, wherein the at least one outlet configured to collect effluent is configured such that the effluent can be collected at different time points.

11. The organ-chip model of claim 1, wherein cell culture media and collection reservoirs are utilized such that passive diffusion can provide the cell culture media to cells without active transport of fluid using a syringe pump.

12. The organ-chip model of claim 1, wherein each cell culture chamber of the plurality of cell culture chambers are configured to be filled to different heights to allow control over diffusion.

13. The organ-chip model of claim 1, further comprising an additional layer comprising at least one culture media reservoir integrated on top of the organ-chip model, and wherein the at least one culture media reservoir comprises an inlet and outlet aligned together.

14. The organ-chip model of claim 11, wherein the at least one culture media reservoir is configured to be periodically filled with at least one of new culture media or biochemicals.

15. The organ-chip model of claim 12, wherein the biochemicals are selected from the group consisting of drugs, harmful substances, and combinations thereof.

16. The organ-chip model of claim 1, wherein fluorescent tagging of cells being grown in the organ-chip model is conducted to visualize cells migrating between the plurality of cell culture chambers.

17. The organ-chip model of claim 1, wherein immunostaining of cells within the organ-chip model is conducted via loading biochemicals for immunostaining of the cells through at least one inlet or a culture media reservoir.

18. The organ-chip model of claim 1, wherein a first cell culture chamber is loaded with a first cell-type and an adjacent cell culture chamber is loaded with second cell-type, wherein the cell-type is selected from the group consisting of amnion epithelial cells (AEC), amnion mesenchymal cells (AMC), chorion mesenchymal cells (CMC)/chorion trophoblast (CT), decidua parietalis cells, decidua basalis, syncytiotrophoblast, cytotrophoblast, HUVEC cells and combinations thereof.

19. The organ-chip model of claim 1, wherein at least one microfluidic channel of the arrays of microfluidic channels is filled with extracellular matrixes.

20. The organ-chip model of claim 1, wherein the plurality of cell culture chambers comprises at least two cell culture chambers.

21. The organ-chip model of claim 1, wherein the plurality of cell culture chambers comprises at least four cell culture chambers.

* * * * *